United States Patent [19]

Peyton et al.

[11] 4,414,566
[45] Nov. 8, 1983

[54] SORTING AND INSPECTION APPARATUS AND METHOD

[75] Inventors: John J. Peyton, Santa Barbara; Robert L. Thomason, Corona del Mar; Hubert W. Evinger, Tustin, all of Calif.

[73] Assignee: Industrial Automation Corporation, Goleta, Calif.

[21] Appl. No.: 250,780

[22] Filed: Apr. 3, 1981

[51] Int. Cl.³ .............................................. H04N 7/18
[52] U.S. Cl. ................................... 358/101; 198/340; 209/524; 209/939; 250/223 B; 356/394; 358/93; 358/106; 358/107; 364/728; 382/42
[58] Field of Search ............... 358/93, 101, 106, 107; 364/728, 478, 514–517, 705; 198/340; 209/522, 524, 526, 528, 939; 250/223 B; 356/240, 394, 71; 382/42

[56] References Cited

U.S. PATENT DOCUMENTS

| | | | |
|---|---|---|---|
| 2,800,226 | 7/1957 | Drennan | 250/223 B |
| 3,358,552 | 12/1967 | Schneider | 250/223 B |
| 3,411,625 | 11/1968 | Calhoun | 209/524 |
| 3,430,766 | 3/1969 | Stone | 209/524 |
| 3,585,513 | 5/1969 | Lucas | 329/117 |
| 3,947,628 | 3/1976 | Alien | 358/93 |
| 3,955,179 | 10/1976 | Planke | 250/223 B |
| 3,997,780 | 12/1976 | Waehner | 250/223 B |
| 3,997,781 | 12/1976 | Messman | 250/223 B |
| 4,002,823 | 1/1977 | Van Oosterhout | 358/106 |
| 4,026,656 | 5/1977 | Kusz | 250/223 B |
| 4,051,366 | 9/1977 | Gordon | 250/223 B |
| 4,055,834 | 10/1977 | Planke | 250/223 B |
| 4,074,130 | 2/1978 | Messman | 250/223 B |
| 4,148,062 | 4/1979 | Kamin | 358/105 |
| 4,164,728 | 8/1979 | Marsh | 364/728 |
| 4,244,650 | 1/1981 | Garfunkel | 250/223 B |

Primary Examiner—Howard Britton
Attorney, Agent, or Firm—Blakely, Sokoloff, Taylor & Zafman

[57] ABSTRACT

Sorting and inspection apparatus and methods which may be used for the identification and separation of articles of different characteristics, or the inspection of articles of similar characteristics to reject those of below minimum standards. A typical system will include a transport system for individually transporting the articles past a television camera so that the camera may view the distinctive portions of the articles to be sorted or the area of the articles to be inspected. The output of the television camera is digitized based upon the number of transitions of light to dark (or dark to light) in the scan lines. A correlator then performs a specialized correlation between the digitized image and various previously digitized images representing the different items being sorted or inspected, to determine which of the previously stored images best correlates with the digitized image from the television camera. A second correlation may be done using a different correlation technique, if desired, to make the final decision based upon the extent of differences between the prestored digitized images and the digitized image from the television camera. The prestored digitized images may be initially created or stored by placing an article with the characteristic to be recognized in front of the television camera and then recording the digitized image. Many refinements and alternate embodiments are disclosed.

39 Claims, 36 Drawing Figures

IAC CORRELATOR
SYSTEM DIAGRAM

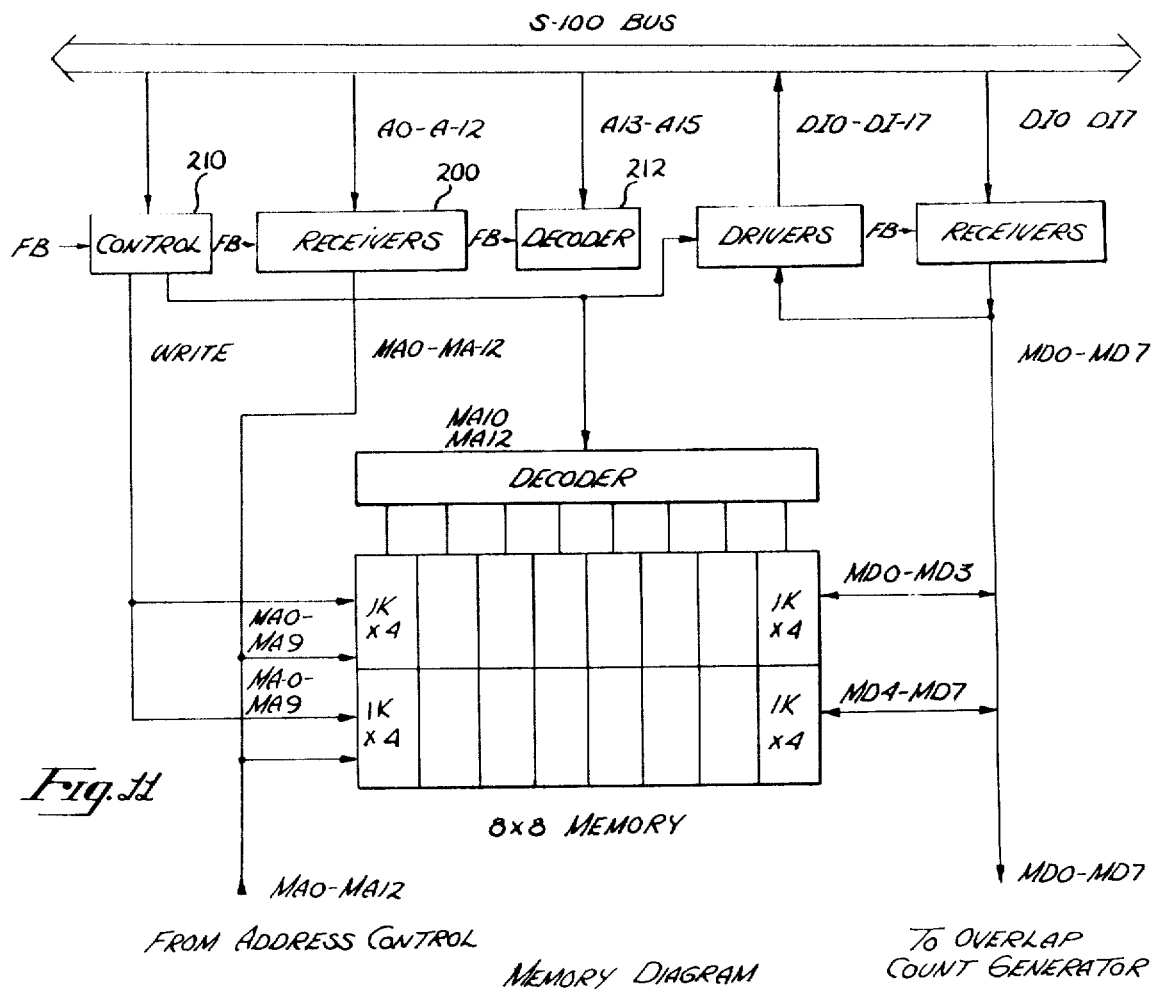

LEFT

Fig. 14b RIGHT

Bottom Left

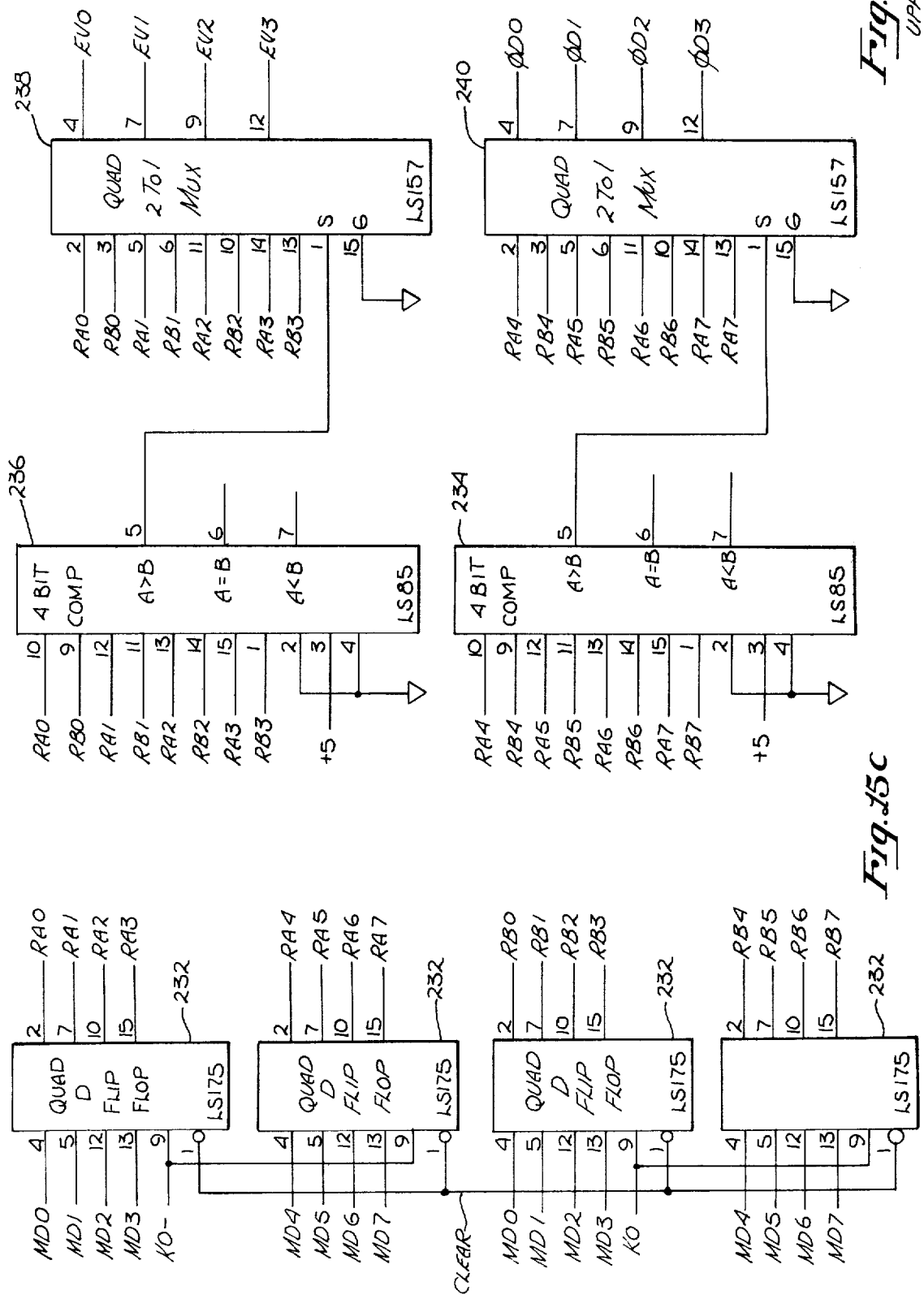

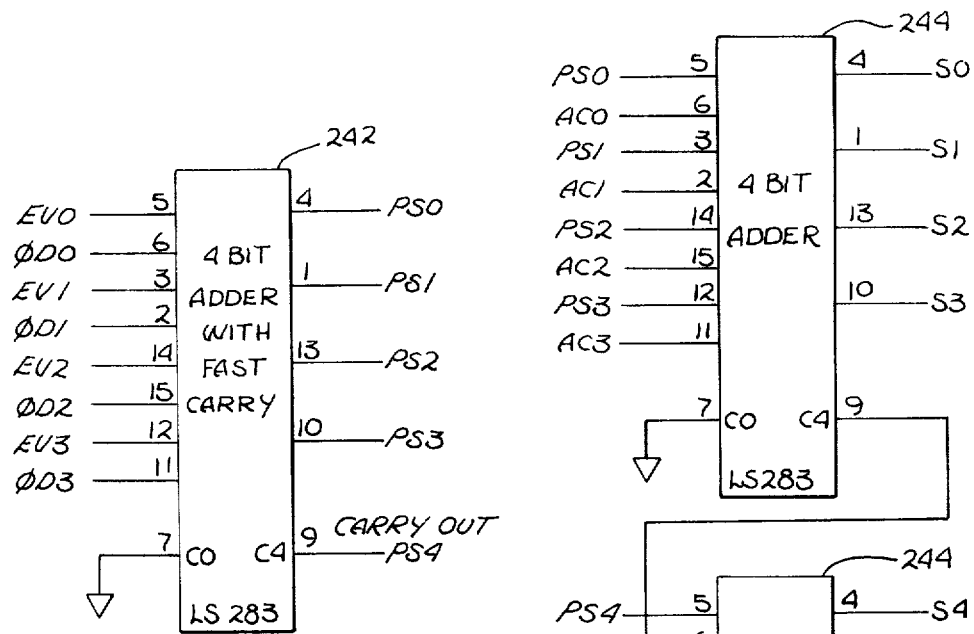
*Fig. 15d*
upper RT
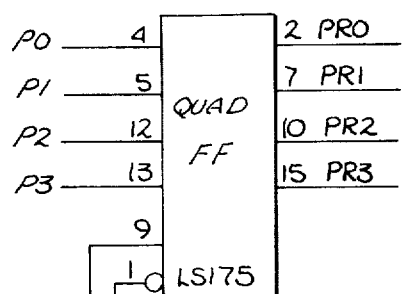
*Fig. 15e*
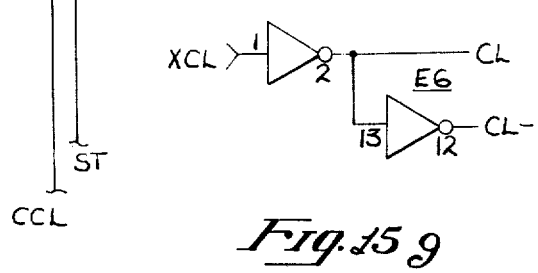
*Fig. 15f*
*Fig. 15g*

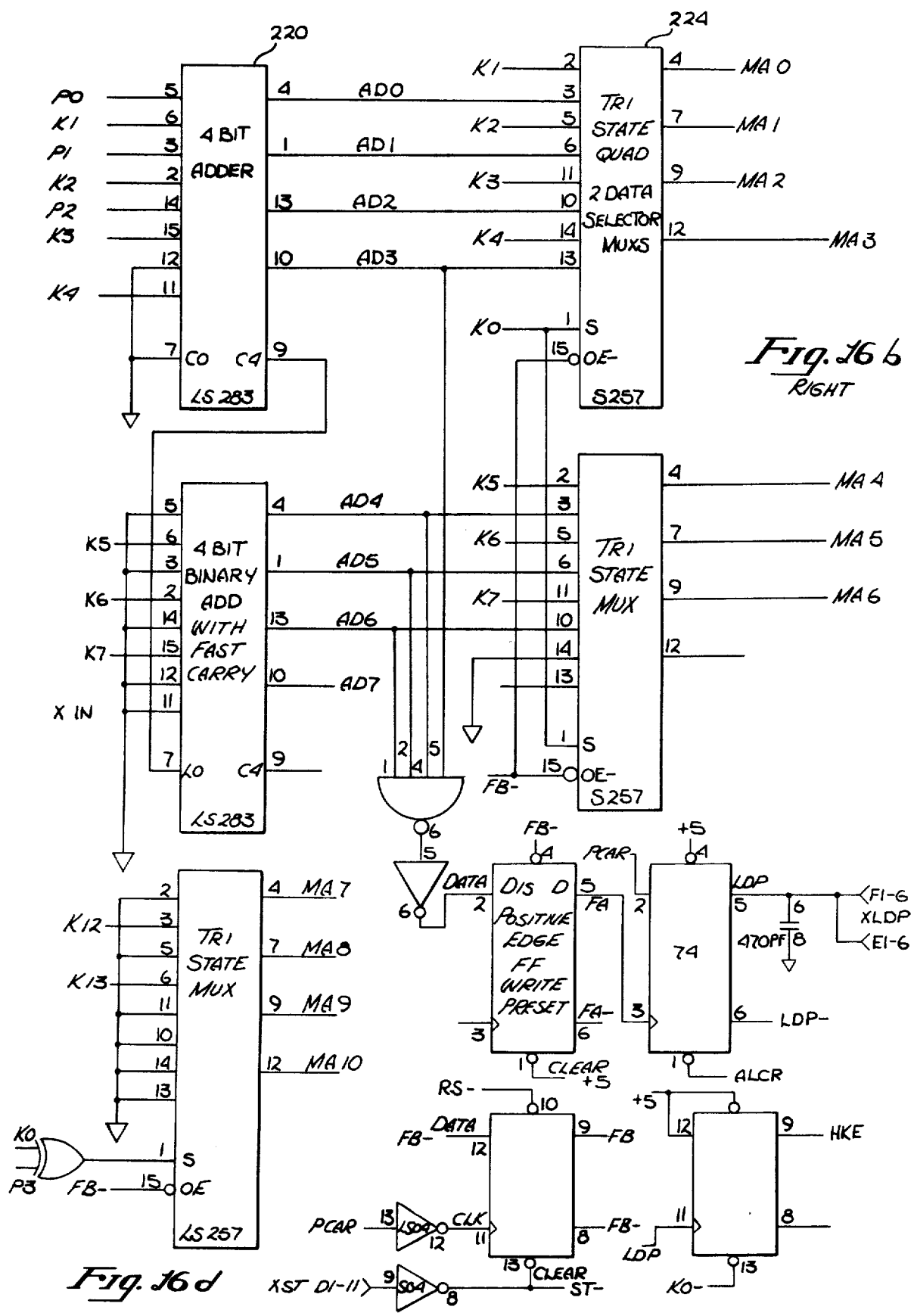

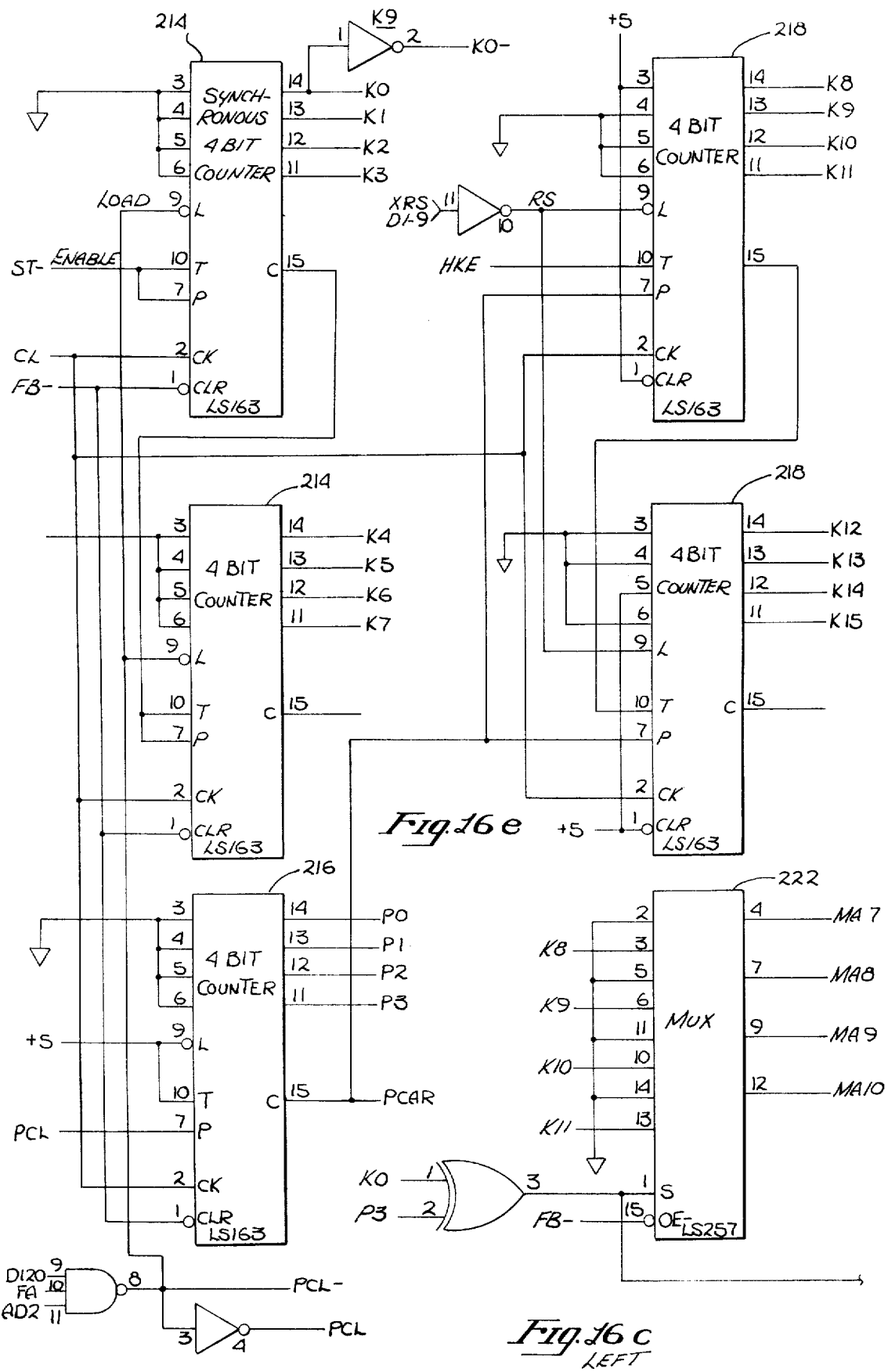

SORTING AND INSPECTION APPARATUS AND METHOD

BACKGROUND OF THE INVENTION

1. Field of the Invention

The present invention relates to the field of automated sorting and inspection apparatus.

2. Prior Art

Various types of automated or semiautomated sorting and inspection apparatus and methods are well known in the prior art. The assignee of the present invention, for example, has manufactured and sold equipment for automatically sorting containers, such as by way of example, returnable soft drink bottles. That apparatus includes a transport system for receiving bottles from an inlet conveyor and for releasing the bottles, based upon a determination of their character, onto any of multiple output conveyors. Identification of the bottles is done by using various sensors to sense readily identifiable characteristics of each bottle in the system as it passes the sensors. For instance, feelers may sense the bottle height or bottle diameter, color sensitive photo optical sensors may sense glass color, etc. Typically the sensors are disposed along or around the transport system so that the sensing of a final characteristic identifying a particular bottle will immediately result in the discharge of that bottle onto the adjacent output conveyor. Such systems operate well under certain conditions, though have various limitations in terms of setup and adjustment time, and of course cannot be effectively used to separate bottles which cannot be characterized by relatively gross, easily sensed parameters. In addition, such devices lack certain flexibility, even when all bottles to be separated have detectable differences, as those detectable differences sometimes pedetermine the order in which the bottles can be identified and thus the order in which they will pass to the respective output conveyors, contrary to an otherwise desired order of output.

Devices of the foregoing type and/or related devices are disclosed in U.S. Pat. Nos. 2,800,226, 2,821,302, 3,358,552, 3,411,625, 3,430,766, and 3,589,513.

U.S. Pat. Nos. 3,997,780, 3,997,781, 4,051,366, and 4,074,130, all filed on the same data, relate to a system for orienting labeled containers so that the labeled containers in a six pack will all be oriented with the labels facing outward. The general system operates on 24 bottles simultaneously, using 24 lenses feeding optical fiber bundles direction to a vidicon camera. The bottles are rotated, and for each of the spinning bottles, the vidicon camera output is quantized, stored and compared repetively over successful cycles, with an eight-bit pattern of four digital "dark" bits followed by four digital "white" bits, a match indicating that a label edge has passed the sensing station several cycles previously so that the bottle may be stopped in a desired position following a settable delay. In essence, the vidicon camera is merely providing a device for multiplexing the 24 sensor signals so that the overall system can sense the edge of a predetermined label on 24 rotating bottles, all of the same bottle and label design. In a second embodiment, photo detectors replace the light pipes and vidicon camera, a serial memory replaces the random access memory used in the data reduction system of the first embodiment, and the label patterns are sensed with optional "Don't care" bits to allow for a fixed predetermined maximum inaccuracy in the sensing.

In U.S. Pat. No. 3,955,179, a system is disclosed using multiple light sensors, fixed at predetermined locations to sense certain overall bottle characteristics as bottles pass thereby. Sensor signals are provided to a computer circuit which is programmed to provide an output corresponding to the value of a given bottle passing through the sensing stage. The system is operable on the shadow of the bottle, with a computer programming unit comprising a programming panel which is programmed by selectively providing interconnections by way of switches or connecting plugs between selected row and column lines. The sensors themselves are also adjustable in position so that the system must be manually programmed and adjusted for the various size and shape bottle to be detected.

Finally, U.S. Pat. No. 4,002,823 discloses a method and apparatus for video inspection of articles of manufacture which utilizes a semi-diffused light source positioned adjacent one side of and optically spaced from the article being inspected for and illuminating the article. A video camera is positioned on the opposite side of the article from the diffused light source and scans the illuminated article in order to produce a video signal indicative of the difference in the refraction characteristics of the article to thereby indicate the presence or absence of defects in the glass where sampled. The video signal is appropriately filtered and then coupled to a peak detector for detecting flaws of unacceptable magnitudes.

BRIEF SUMMARY OF THE INVENTION

Sorting and inspection apparatus and methods which may be used for the identification and separation of articles of different characteristics, or the inspection of articles of similar characteristics to reject those of below minimum standards. A typical system will include a transport system for individually transporting the articles past a television camera so that the camera may view the distinctive portions of the articles to be sorted or the area of the articles to be inspected. The output of the television camera is digitized based upon the number of transitions of light to dark (or dark to light) in the scan lines. A correlator then performs a specialized correlation between the digitized image and various previously digitized images representing the different items being sorted or inspected, to determine which of the previously stored images best correlates with the digitized image from the television camera. The initial correlation is tailored to generally look for areas of similarity, though in some cases where the best correlation is not significantly better than the second best correlation, a second correlation may be done using a different correlation technique to make the final decision based upon the extent of differences between the closer prestored digitized images and the digitized image from the television camera. The prestored digitized images may be initially created or stored by placing an article with the characteristic to be recognized in front of the television camera and then recording the digitized image. Many refinements and alternate embodiments are disclosed.

BRIEF SUMMARY OF THE DRAWINGS

FIG. 11 is a block diagram of the table memory.

FIG. 12 is a block diagram of the overlap count generator.

FIGS. 15a, 15b, 15c, 15d, 15e, 15f, 15g, 16a, 16b, 16c and 16d are the circuit diagrams of the remaining portions of the correlator.

DETAILED DESCRIPTION OF THE INVENTION

Figure 1:
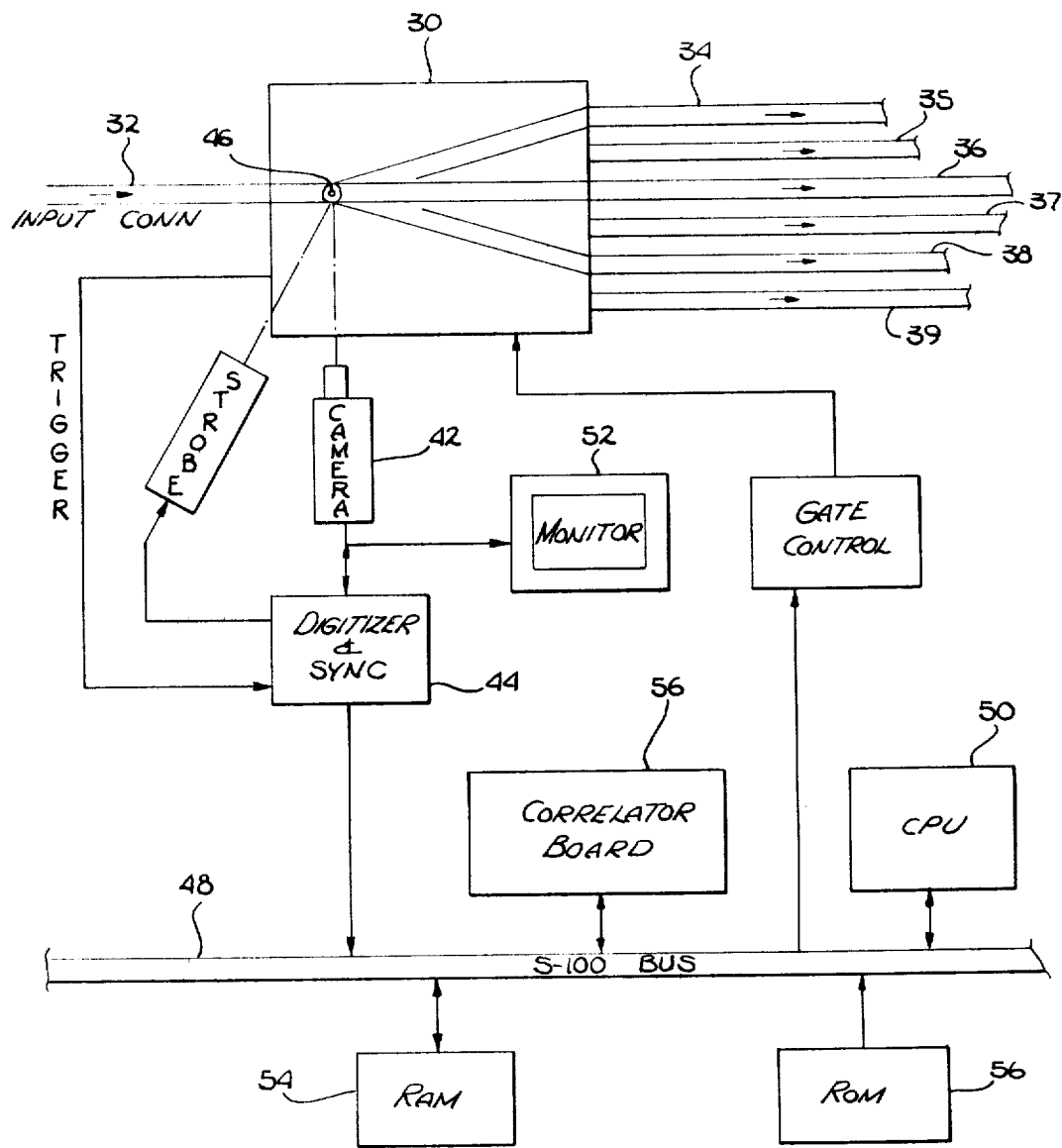
FIG. 1 is a block diagram of the preferred embodiment of the present invention.

The present invention is best described with reference to a specific embodiment thereof directed to the solution of a specific problem, as such preferred embodiment is exemplary of most of the elements of other embodiments readily useful for other purposes. The particular embodiment disclosed herein is directed to the automatic sorting of returnable soft drink bottles presented initially in unsorted fashion on a conveyor line. Such bottles generally have already undergone some form of gross sorting, in that large and small bottles will not be intermixed, though the stream of bottles of all approximately the same size will generally include a mix of a number of different types of bottles, some of which may be quite different from each other, such as Coke and Pepsi bottles, and some of which may be quite similar to each other, such as Sprite and Diet Sprite bottles. In any event, such bottles conventially carry a permanent trademark and/or decoration on the sides thereof, extending over 180 degrees or less of the circumference of the bottle, and repeating on the opposite side thereof. Consequently, the bottles to be sorted in this embodiment will have visually identifiable differences viewable from one side thereof.

In the system to be described in detail herein, a bottle transport system is provided which receives the bottles directed thereto on an input conveyor and individually grasps and transports the bottles on a starwheel to carry the bottles in a circumferential trajectory. A number of outlet conveyors are provided at different points around the trajectory of the starwheel so that a bottle, when released by the starwheel system adjacent one of the outlet conveyors, will pass into and travel along that conveyor. Thus a bottle, once identified, will be released by the starwheel system adjacent the preassigned outlet conveyor for that bottle type, thereby passing in sorted fashion onto the prescribed conveyor.

For purposes of identifying the bottles on the starwheel system to determine the appropriate release point for each bottle, a television camera is provided to the side of the starwheel adjacent the input conveyor, so as to be positioned to view the side of each bottle just after pickup by the starwheel. The camera is set to view the label region on each bottle, as each bottle passes a specific inspection point on the transport system. Because of the finite distance between the bottles being inspected and the television camera and lens system associated therewith, the camera will view slightly less than 180 degrees of the bottle, and thus will not quite view a complete label, depending on label size and bottle orientation. Further, the curvature of the bottle will tend to compress the image of the label as seen by the video camera, particularly adjacent the edges of the image. Since in the preferred embodiment the bottles are not given any specific angular orientation, the portion of the label which suffers this compression in its image as perceived by the video camera will be essentially random, though as small subsequently be seen, the system of the present invention is substantially insensitive to that compression. Finally, in a high speed system, a strobe light or a pair of strobe lights is used to strobe the bottle as each reaches the inspection point to provide a better and faster response to the video camera. Also, because of the curvature of the bottle and the single or at least limited numbers of strobe lights, different portions of the label image as perceived by the video camera will have different intensities, though as shall subsequently be seen, the system of the present invention has minimal sensitivity to such variations.

Many of the foregoing characteristics of the image perceived by the video camera could be minimized or overcome by more elaborate lens and lighting systems. In addition, the label as viewed by the camera could be "unwrapped" by mirror and/or complicated lens systems, and the bottles could be angularly oriented so that the label is always viewed face on. However, one of the features of the present invention is that highly reliable and accurate operation is achieved without the expense and mechanical complexity of the additional apparatus and operations to achieve the foregoing.

The video camera used in the preferred embodiment is a standard (U.S.) video camera using interlaced scanning, having a field frequency of 60 Hz (i.e., providing 60 half frames per second) and a frame frequency of 30 Hz. When a bottle reaches the inspection point as indicated by a sensor on the tranport system and the stobe is fired, each line of 240 lines in a field is digitized to provide a four bit binary number for each line representing the number of transitions of light to dark in that line of the image. Thus in this embodiment, a maximum of 15 such transitions per line is allowed, which has been found to be entirely satisfactory for reading bottle labels. It should be noted at this point that since the digitized signal for any line is only indicative of the member of transitions (of a given threshold) in that line of the image, and is not sensitive to the position of any of the transitions along the line, the digitized information for each line is relatively insensitive to the angular orientation of the bottle and the horizontal compression of the label image along the edges thereof.

The digitized information for each field is temporarily stored in a memory having the capability of storing 63 other such digitized images. For reference, the bottle at the inspection point shall be referred to as the target bottle with the corresponding digitized image of the target bottle being referred to as the target image, target data or, in table form, the target table. The other digitized images stored in the remaining 63 memory blocks are generally referred to as library images, library data, or library table, as this data represents prerecorded data on the various types of bottles to be sorted, against which the target data will be compared to determine which of the various types of bottles to be sorted is at the inspection point.

In particular, a high speed correlator is used to perform a form of correlation between the target table and each of the library tables on a line by line basis to determine which of the library tables best correlates with the target table. The form of correlation used in the preferred embodiment is not a true correlation, but rather a modified type of correlation selected because of its computational simplicity (i.e., susceptible of being performed at high speed) and adequate accuracy in the result. In particular, for each line of the target data and the corresponding line of one of the library tables, the four bit binary number of a target data line is compared with a four bit number of the library table data line, with the smaller of the two numbers being added to a first running total for that correlation. In addition, the 240 four bit binary numbers for the target table are accumulated to provide a second running total, and the 240 four bit binary numbers for the library table are accumulated to provide a third running total. The correlation factor between the target table and the particular library table under consideration is equal to the first running total divided by either the second or third running total, whichever is higher. In equation form, the correlation coefficient may be stated as follows:

$$CC = \frac{\sum_{n=1}^{240} (T_{tn} \text{ or } T_{ln}, \text{ whichever is lower})}{\sum_{n=1}^{240} T_{tn} \text{ or } \sum_{n=1}^{240} T_{ln}, \text{ whichever is higher}}$$

Where
CC = correlation coefficient
$T_{tn}$ = number of transitions in line n of the target table
$T_{ln}$ = number of transitions in line n of the library table under consideration The foregoing equation is based on the following:

If the number of transitions in any table (target or library) is plotted as a bar chart by plotting line number along one axis and providing a bar of unit width for each line number in the direction of a second axis, the bar having a length proportional to the number of transitions for that line in the table, a unique curve characteristic of that particular table will be obtained. In regions above or below the corresponding label position on the bottle, the number of transitions may be zero, with different label segments providing different numbers of transitions to provide unique curves in the non-zero portions. If one were to overlay a similar table constructed for a different bottle type, the curve shape, of course, would be different, being unique for the different bottle type of the second table. Portions of the areas under the two bar charts may overlap (though not necessarily so), but in general the size and shapes of the areas will be substantially different for each bottle type.

Referring back to the foregoing equation for calculating the correlation coefficient, it will be noted that the total, for all lines, of the number of transitions of each line of the library table under consideration (the second running total) merely represents the total area under the bar chart curve for the respective library table. Similarly the total, for all lines, of the number of transitions in each line of the target data (the third running total) merely represents the area under the bar chart curve for the target table. Thus the denominator of the foregoing equation for the correlation coefficient merely represents the area under the bar chart curve for the target table or the library table under consideration, whichever is larger. The numerator on the other hand, compares each line of the target table with a corresponding line of the library table, and by taking the lower of the two, effectively only considers the overlap of the respective region of the two curves. By totalling the overlaps for each line, the total overlap area is obtained. Thus the equation for the correlation coefficient hereinbefore given is effectively the following:

$$CC = \frac{\text{total overlap area}}{\text{larger total area}}$$

It may be seen from the foregoing equation that if the target table is identical with the particular library table under consideration, the two bar chart curves will be identical, that is, they will exactly overlap each other and both will have the same total area, specifically an area equal to the overlap area. As such, the correlation coefficient would be one, showing the best possible correlation between the two tables as desired. If, on the other hand, the target table and the library table both had a majority of lines indicating no transitions therein, and the lines of the target table having transitions therein are different lines from those in the library table having transitions therein, the total overlap area will be zero, so that the correlation coefficient is zero. This illustrates the range of the correlation coefficient from zero to one, and is also introductory to another aspect of the present invention. In particular, for aesthetic reasons, bottle labels are generally aligned with the horizontal fairly accurately, i.e., do not have significant skew, though may vary as much as plus or minus ⅛ of an inch or more in elevation, as elevational variations are not visually objectionable. Accordingly, theoretically, if the library table and the target table are for the same bottle type, but there were substantial elevational differences between the label used to construct the library table and the label on the target bottle, the correlation coefficient using the foregoing equation will be less than one by an amount depending upon the particular label in question and the exact elevational differences. Obviously, better correlation could be obtained if the table for the bottle having the lower label could be "lifted" or the table for the same type bottle with the higher label could be "lowered". This effect can be substantial as some bottles such as Sprite and Diet Sprite have labels which are identical except for small portions thereof, so that correlation errors caused by such vertical offsets may result in misidentification of the bottle type. In order to avoid this, the present invention performs the foregoing correlation, not only by comparing each line of the target table with the corresponding line of a library table under consideration, but also performs for each library table fifteen other numerator calculations for that library table, these calculations representing a downward shift of the library table with respect to the target table, and then a downward shift of the target table with respect to the library table. A chart showing the relative offset between the target and library lines for the sixteen calculations (passes zero through fifteen) is presented below.

| PASS | TARGET LINE | LIBRARY LINE |
|---|---|---|
| 0 | 0 | 0 |
| 1 | 0 | 2 |
| 2 | 0 | 4 |
| 3 | 0 | 6 |
| 4 | 0 | 8 |
| 5 | 0 | 10 |
| 6 | 0 | 12 |
| 7 | 0 | 14 |
| 8 | 0 | 0 |
| 9 | 2 | 0 |
| 10 | 4 | 0 |
| 11 | 6 | 0 |
| 12 | 8 | 0 |
| 13 | 10 | 0 |
| 14 | 12 | 0 |
| 15 | 14 | 0 |

It will be noted that pass zero and pass eight are identical, and accordingly, one of them is redundant. This is merely a result of the particular implimentation used and could be eliminated if desired, though is relatively inconsequential in the overall scheme. Also, it will be noted that in effect, the shifting through the sixteen passes is by two lines at a time, representing a maximum shifting of plus or minus 14 lines. If the 240 lines in each table represent approximately a six inch vertical view of the bottles, plus or minus 14 lines represents plus or minus 0.35 inches, taken in 0.05 inches increments. Also, since pass zero (and pass eight) consider all 240 lines of both tables whereby the numerator in the equation for the correlation coefficient is comprised of the sum of 240 terms, the number of terms reduces for the other passes, being 226 for passes seven and fifteen. This, too, is a result of the particular implementation of the present invention, as it would perhaps be better to confine each of the multiple passes to the same number, such as 226, though in practice this refinement has not been found necessary. The denominator for the correlation coefficient equation, of course, is the same for each pass. As shall be seen in a subsequent description, the high speed correlator is configured to retain the highest numerator (representing the best correlation) obtained in the 16 passes so that the ultimate correlation coefficient used between the target table and a specific library table is the highest correlation coefficient found during any of the sixteen passes for that table. This, of course, is repeated for each of the 63 potential library tables (i.e., for a total of 1,008 times) to provide 63 correlation coefficients, each corresponding to the correlation between the target table and a respective one of the library tables.

Having now given a more detailed general overview of the invention, further details of the general organization of the invention may be seen with reference to FIG. 1. The transport system 30 may be characterized by a single input conveyor 32 and a plurality of output conveyors 34 through 39, each of which may receive a bottle from the input conveyor 32 depending upon controls provided to the transport system 30 by the gate control 40. A video camera 42 is constantly viewing a fixed position in the transport system and providing a composite video signal to a digitizer and synchronizing signal circuit 44. The composite video signal, of course, contains not only the video information but also contains the horizontal and vertical sync signals so that the digitizer and sync circuit 44 will synchronize itself to the composite video signal and remain synchronized between target data entry.

When a bottle such as bottle 46 reaches the appropriate position for viewing by the camera 42 an appropriate sensor on the transport system will provide a trigger signal to the digitizer and sync circuit 44, which in turn will fire the strobe, digitize 240 lines of the video signal and provide the digitized data on a line by line basis to the S-100 bus 48. The S-100 bus is a 100 pin bus first introduced by MITS, Inc. on their Intel 8080 based Altair kit, and has now become a fairly standard bus structure for microcomputer systems. It was chosen for use in the preferred embodiment because of the availability of single board microcomputers which directly interface with the bus. In that regard, a Chromemco single board computer is used for the CPU 50, which provides much of the communication control, some of the data reduction, and other functions, such as generation of gate control signals, creation of library tables, etc.

A closed circuit TV monitor 52 may be used to monitor the image provide by the camera 42, if desired. In general, a monitor probably will only be used for set-up and/or trouble shooting, as its presence is not required for the normal operation of the system. However, as an added feature, the digitizer and sync circuit 44 contains an additional circuitry which modifies the composite video signal so that the monitor 52 may display not only the image of the bottle as viewed by the camera, but also a form of bar chart hereinbefore described. In particular, as previously mentioned, the digitizer counts the number of light to dark transitions in each of the 240 individual lines of the bottle image and provides a four bit binary number representing the number of transitions (zero to fifteen) in that line. The digitizer and sync circuit 44 contains timing and control circuitry so that during part of each of the 240 horizonal line sweeps, the bottle image is digitized as stated, but that during the remainder of each horizontal sweep, a counter containing the digitized count for that line is clocked to zero at a given clock rate, during which time the composite video signal is held to a white level. The net result is that the display on the video monitor 52 is of the bottle and label at the left of the screen, with the bar chart previously described displayed at the right of the screen, aligned in elevation with the bottle image.

Also connected to the S-100 bus in the preferred embodiment is a memory 54 (preferably random access memory [RAM], though the library tables could be stored in ROM or other non-volatile memory if desired) for storing the digitized target table and the previously stored 63 library tables, and a high speed correlator board for calculating the overlap area as part of the calculation of the correlation coefficients. The central processing unit 50 of course will either use part of memory 54 or other separate memory on the S-100 bus for its own temporary storage in accomplishing its computational functions for control and other purposes. Finally, a read-only memory 56 (ROM) is provided for nonvolatile storage of the system program.

Figure 2:
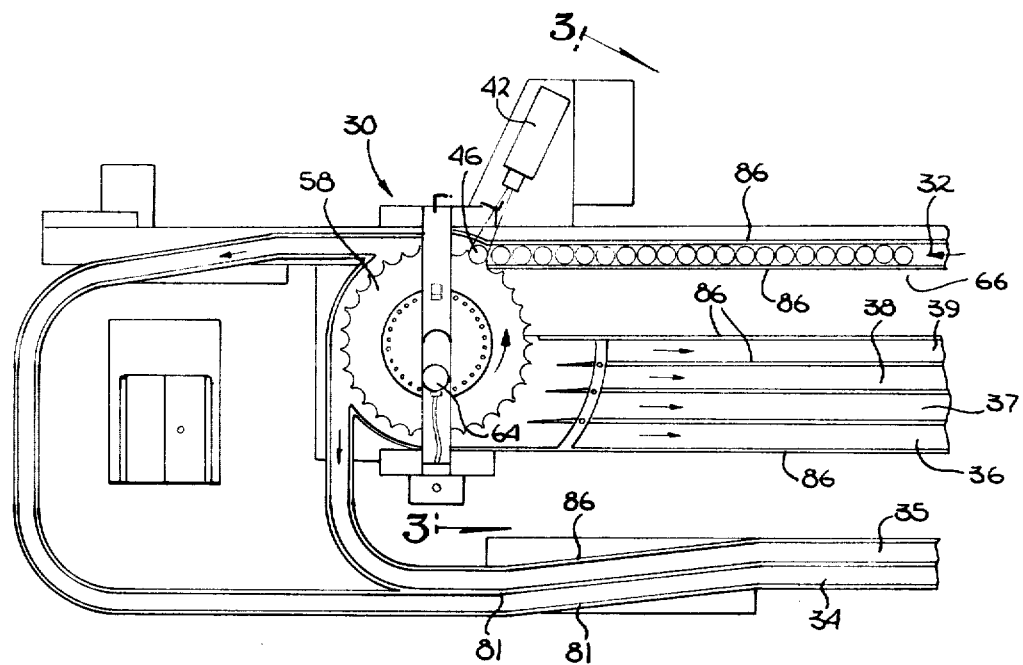
FIG. 2 is a top view of the bottle handling apparatus of FIG. 1, illustrating the camera position therein.
Figure 3:
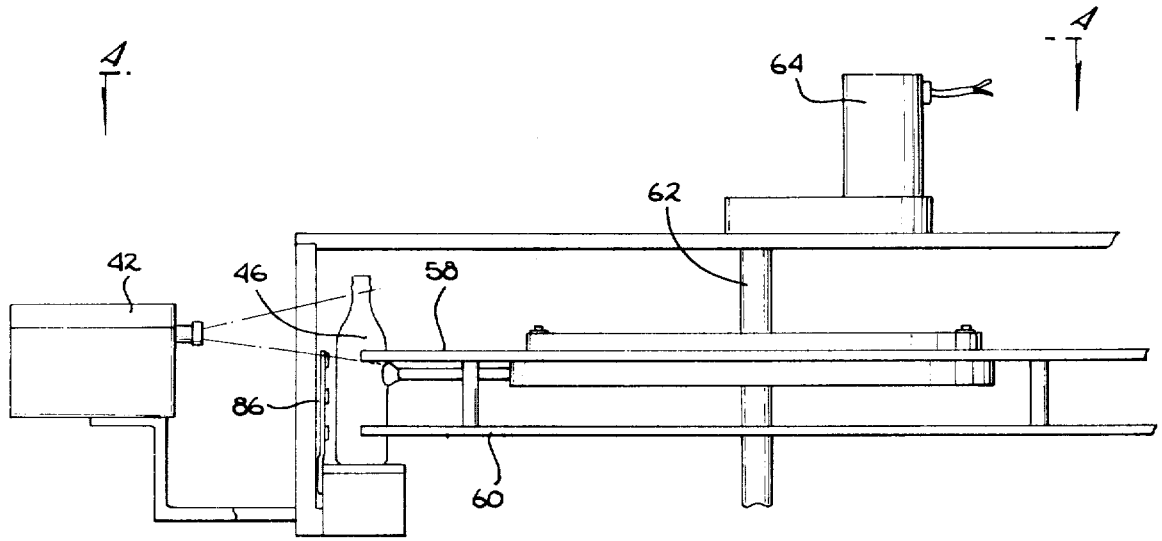
FIG. 3 is a side view taken along line 3—3 of FIG. 2.
Figure 4:
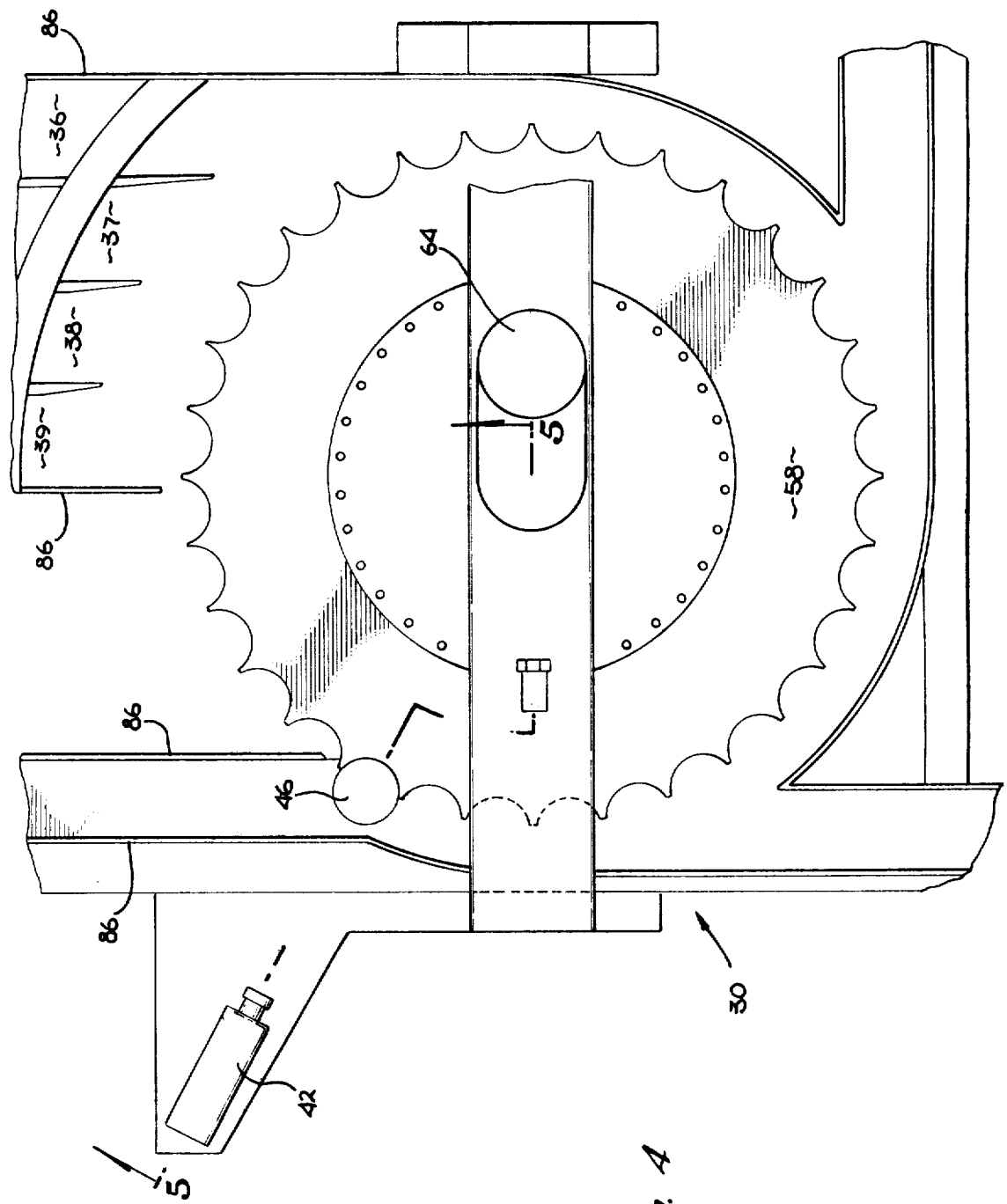
FIG. 4 is a top view taken along line 4—4 of FIG. 3.
Figure 5:
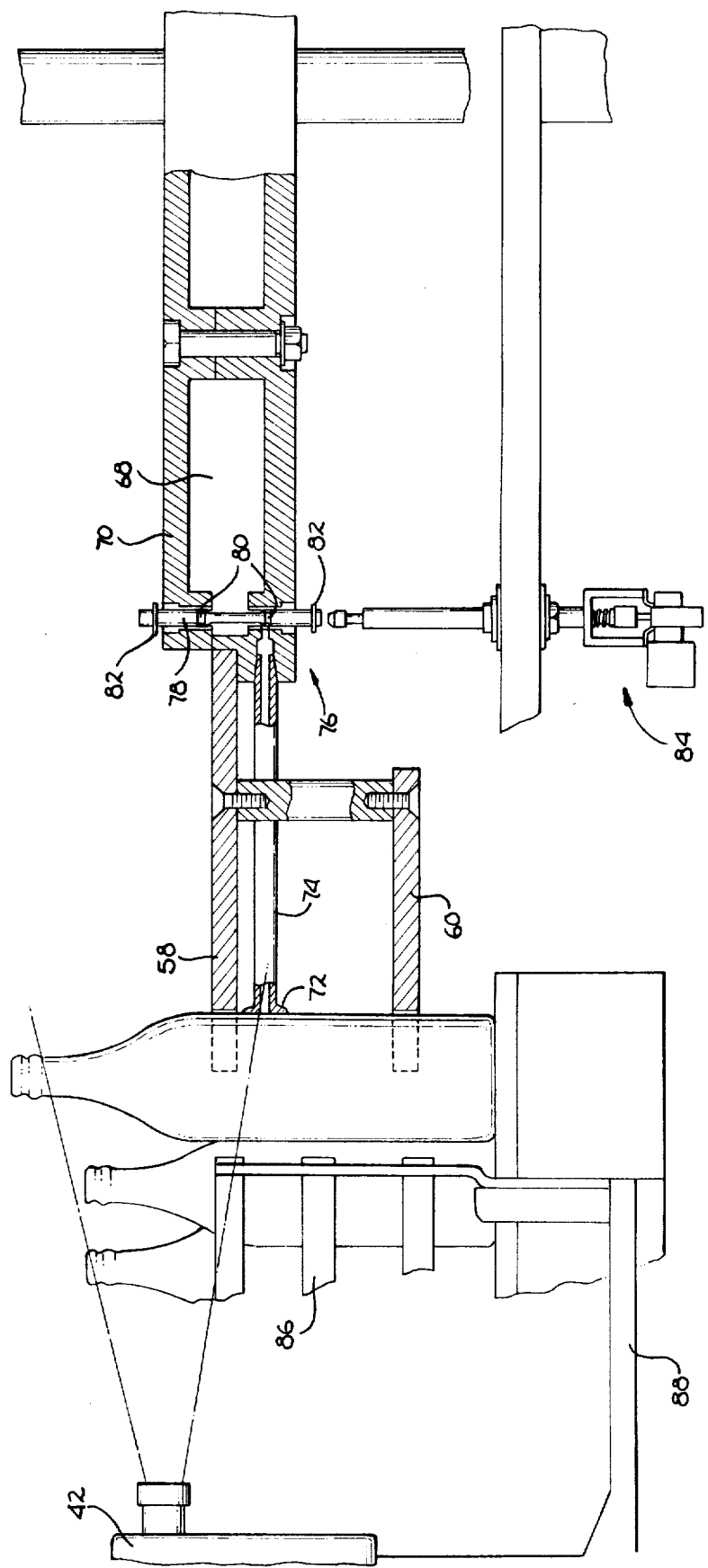
FIG. 5 is a view taken along line 5—5 of FIG. 4.

Now referring to FIGS. 2 through 5, various details of the transport system used with one embodiment of the present invention may be seen. The particular transport system illustrated is the transport system which has previously been manufactured and sold by the assignee of the present invention as part of its series 700 bottle sorting system. As in FIG. 1, the top view of the transport system 30 of FIG. 2 illustrates the input conveyor 32 and the plurality of output conveyors 34 through 39. The input conveyor delivers bottles to a star wheel system comprising an upper star wheel 58 and a lower star wheel 60 (see FIGS. 3 and 5 also) mounted on shaft 62 for rotation about the axis thereof by drive motor 64. In general, such systems are intended to operate with a "full" input conveyor so that once the first bottle feeds properly into a set of pockets in the upper and lower star wheels, all subsequent bottles will be appropriately positioned with respect to each other so as to also smoothly feed into the star wheel system. Accordingly, generally motor 64 will be controlled by one or more sensors such as sensor 66 indicating whether sufficient bottles are backed up on the input conveyor to turn on the star wheel transport system.

The starwheel system contains a vacuum chamber 68 defined by an enclosure 70 (see FIGS. 2 through 4, and particularly FIG. 5) coupled through a rotary coupling (not shown) to a vacuum source. Between the upper starwheel 58 and the lower starwheel 60, and aligned with each set of bottle pockets therein is a vacuum gripper comprising a rubber suction cup 72, supported by a tube-like member 74 in communication of assembly generally indicated by the numeral 76. The valve assembly controlling the vacuum to each vacuum cup 72 is controlled by a valve pin 78, slidable in the vertical direction between limits defined by retaining rings 82. O-rings 80 on the valve pins 78 provide both a seal therefore and frictional restraint of the valve pins so that each pin will remain in any set position until forceably moved to another position. In general, each valve pin is configured so that when the valve pin is down as shown, the respective suction cup 72 will be in communication with region 68, thereby having the vacuum applied thereto to suck the bottle firmly into the bottle pockets on the starwheels 58 and 60. When the valve pin 78 is moved to the upper position, vacuum chamber 68 is no longer in communication with the suction cup 72, but instead, member 74 and therefore suction cup 72 are vented to the atmosphere around the lower portion of the pin 78. Consequently, when a valve pin 78 is in the upper position, bottles will be grasped and thereafter retained in the starwheel until the valve pin is again moved downward to release the bottle. Usually a fixed cam is provided to move each valve pin upward at the bottle pickup point, with solenoid controlled air cylinders 84 being appropriately positioned adjacent the outlet conveyors to force individual valve pins upwards to release bottles at that point upon appropriately timed actuation thereof based upon the identification of the bottles. If desired, a cam can be used at the final outlet conveyor to be sure that all bottles are ultimately released before that set of bottle pockets returns to the bottle pickup point adjacent the inlet conveyor to avoid bottle breakage and jamming in the event of a malfunction for some reason. As previously mentioned, this specific type of transport system is exemplary only, and already being well-known, will not be further described herein except as specifically applicable to the operation of the overall system.

In general, the bottles on the inlet conveyor 32 and on the various outlet conveyors 34 through 39 are confined by siderails 86, though once the bottles reach the pickup point and are grasped by a suction cup, side rails of significant elevation are not required, so that the video camera 42 may have a substantially unobstructed view of the side of the bottle. In general the video camera will be supported on some appropriate support structure 88, preferably physically referenced to the transport system, but adjustable thereon to adjust the height, field of view, etc. for various bottle sizes.

Figure 6:
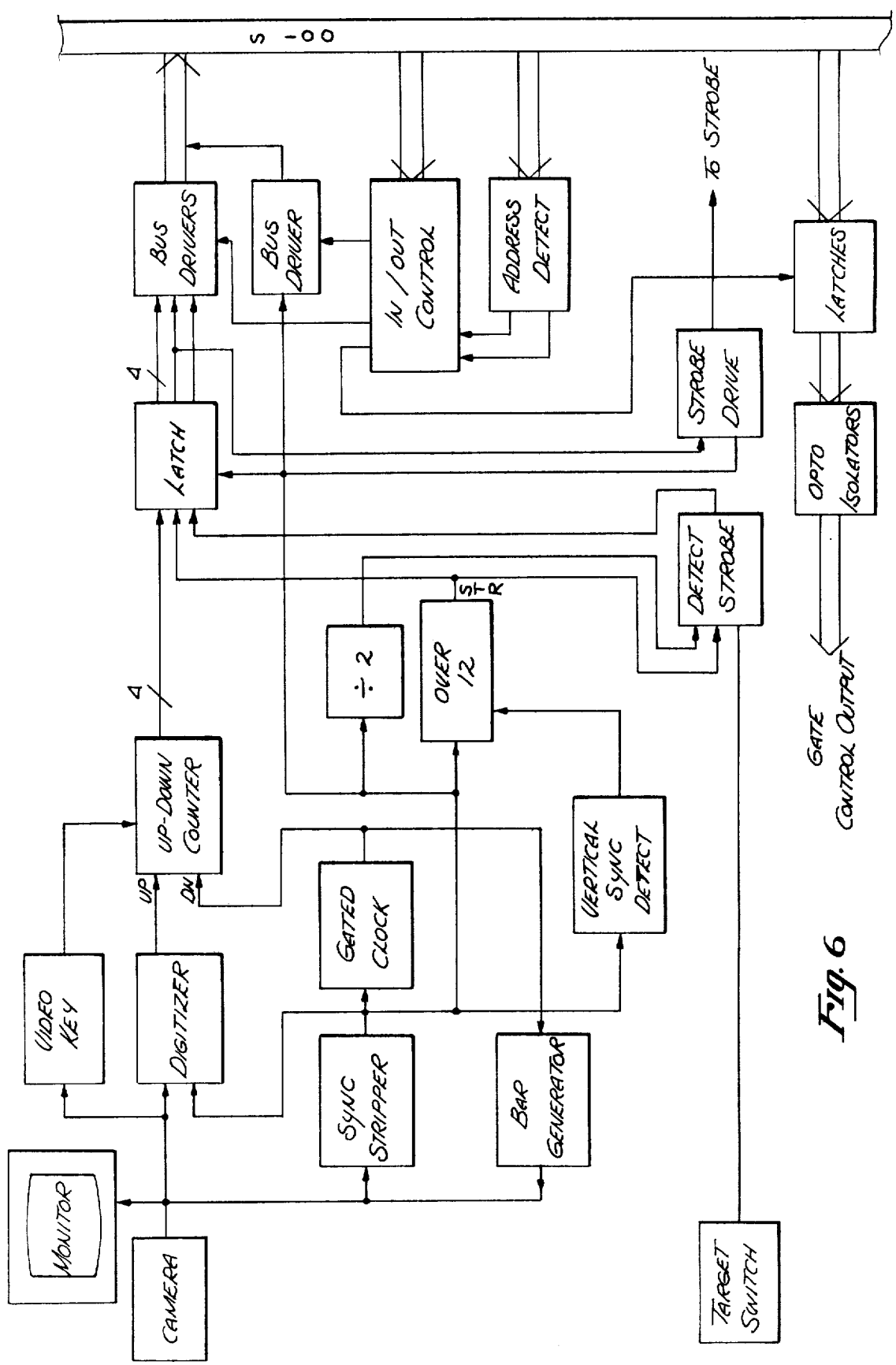
FIG. 6 is a block diagram illustrating the organization of the digitizer and other aspects of the electronic system of the present invention.
Figure 7:
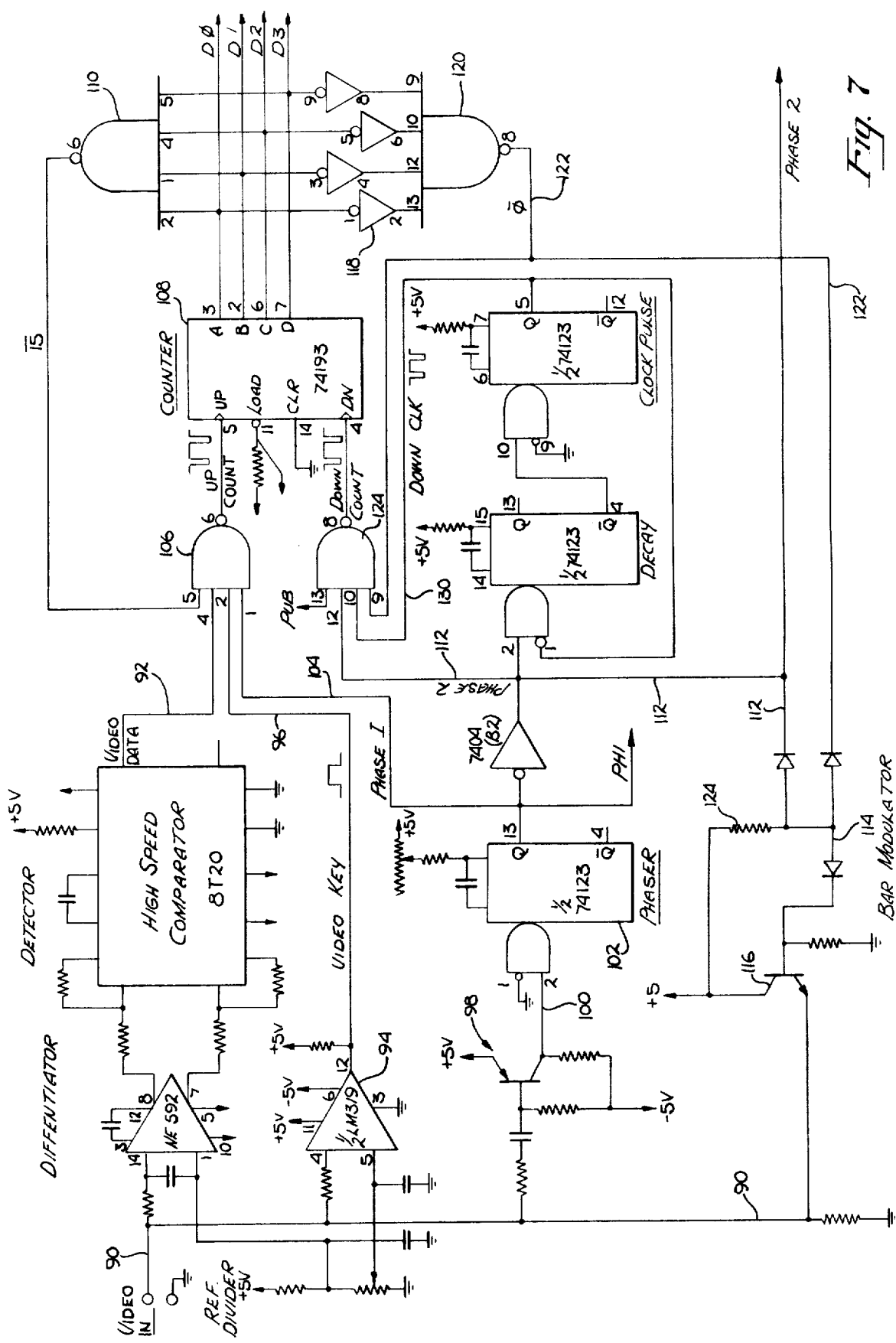
FIG. 7 is a circuit diagram of the digitizer.

Now referring to FIGS. 6 through 9, details of the video digitizing and associated circuitry may be seen. FIG. 6 is a general block diagram of the circuitry of FIGS. 7 through 9, with FIGS. 7 through 9 providing the detailed circuits thereof. The composite video signal from camera 42 on line 90 (FIGS. 6 and 7 is applied to NE 592 differential video amplifier connected as a differentiator with the outputs thereof being coupled to a high speed comparator which, for each transition sensed in the video signal, will provide a pulse output on line 92. The combination of digitizer and high-speed comparator of FIG. 7 essentially provides the function of the digitizer of FIG. 6, the differentiator being used rather than a straight level detector because the differentiator is not generally sensitive to image intensity. In particular, a simple level detector would be sensitive to variations in strobe position and intensity, camera sensitivity, etc., whereas the differentiator is sensitive primarily to the presence of the transitions regardless of the average intensity of the image as reflected by the composite video signal. In that regard, as pointed out before, portions of the image may be lighted better than other portions of the image, though in general, the transition between such regions will not be nearly as abrupt as a light to dark (or dark to light) transition due to the trademark on the bottle, and accordingly, the circuit may be made relatively insensitive to such gradual variations in intensity across the entire width of the bottle image by appropriate choice of differentiator characteristics. In addition, an amplifier 94 connected as a comparator is used to provide a video key signal on line 96 indicating that at least a minimum intensity signal is being received.

In addition to the foregoing, the composite video signal on line 90 is coupled to a sync stripper, generally indicated by numeral 98. The sync stripper circuit 98 is basically a bipolar transistor clipper circuit to provide an output on line 100 indicative of the presence of the horizontal sync signal indicating horizontal retrace. (The horizontal sync signal in the composite video is a "blacker than black" signal which both blanks the beam and signals the reset of the horizontal deflection circuit in the video camera.) The signal on line 100 is applied to a retriggerable one-shot 102, with the output of the one-shot on line 104 being coupled to NAND gate 106. The output of the NAND gate is coupled to the up count input of counter 108, with a four bit output thereof, lines D0 through D3, being NANDed by NAND gate 110 to provide a fourth input to the NAND gate 106. In essence, the differentiator and high speed comparator constantly digitizes the composite video signal on line 90 and provides a pulse train in response thereto on line 92 as one input to the NAND gate 106. A second input to the NAND gate is provided by the video key signal on line 96 which essentially disables the NAND gate 106 during horizontal retrace (because of the blacker than black signal then present) and during a period where the image intensity is generally too low to provide valid information. The triggerable one-shot 102 coupled to the sync stripper is given a predetermined time constant so that the signal on line 104 forming another input for NAND gate 106 represents an enable signal during horizontal retrace (approximately five microseconds) and for approximately one-half of the horizontal sweep time 58.5 microseconds, i.e., approximately 30 microseconds. Thus, the combination of the video key signal on line 96 and the phase 1 (PH1) signal on line 104, provide enable signals to the NAND gate 106 which enable the gate at the beginning of each horizontal sweep for approximately one-half of that sweep. Finally, the fourth input to NAND gate 106 from NAND gate 110 provides a disable signal to NAND gate 106 when the outputs D0 through D3 of counter 108 indicate that a count of 15 has been reached. Thus, in summary, counter 108 is enabled for an up count of the video signal transitions during the initial portion of each horizontal sweep, being disabled approximately half way through each horizontal sweep unless earlier disabled by the achievement of a count of 15.

During this initial portion of each horizontal sweep, the phase 1 signal on line 104 is high, and accordingly, the phase 2 signal on lines 112 is low. This holds line 114 low, thereby holding transistor 116 in the off condition. However, at the end of this initial period when the signal on line 104 goes low, the signal on line 112 goes high. If no transitions were detected during the initial period of that sweep, the combination of inverters 118 and NAND gate 120 provide a low state signal on line 122 which disables NAND gate 124 and also holds line 114 low through the diode between lines 114 and 122. On the other hand, if any transitions have been detected during the initial portion of the horizontal sweep, line 122 will be high during the remaining portion of the horizontal sweep (as will be line 112) thereby turning on transistor 116 through resistor 124. At the same time one shots 126 and 128, coupled as a relatively high frequency high frequency oscillator, provide a down clock signal on line 130 to NAND gate 124. Since the other three signals to the NAND gate are now in an enable state, counter 108 proceeds to count down from whatever digitized value has accumulated therein during the initial portion of the sweep, during which time transistor 116 remains on. This pulls the composite video signal line 90 high or to a bright state, creating a bar (a portion of the bar chart hereinbefore described) to the right of the monitor display of a length proportional to the counts accumulated during the initial portion of that horizontal sweep. In that regard, when counter 108 again counts down to zero, the combination of inverters 118 and NAND gate 120 detect the zero count and disable NAND gate 124 by driving line 122 low, which also turns off transister 116. Thus, during the initial portion of each horizontal sweep, the composite video signal is digitized and accumulated to provide a four bit digitized output signal D0 through D3, with the digitized signal being counted down to zero during the remaining portion of the sweep to alter the composite video signal by the generation of a signal representing a portion of a bar chart corresponding to the digitization of that portion of the bottle label image. This is shown in FIG. 6 wherein the gated clock operating in conjunction with the sync stripper, provides a down count for the up-down couner, and at the same time drives the bar generator which alters the composite video signal on line 90.

Figure 8:
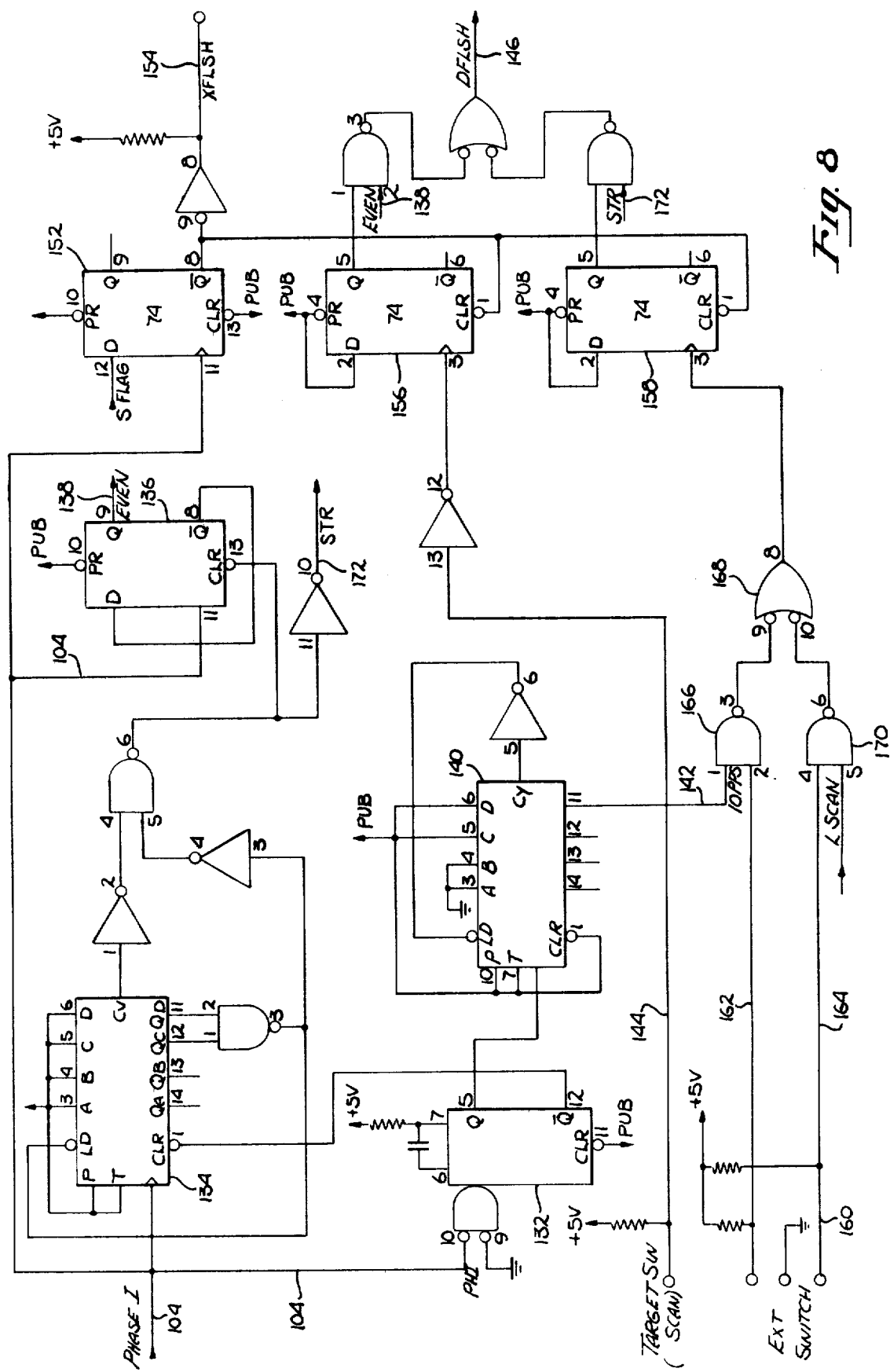
FIG. 8 is a circuit diagram for the scan sync logic.

Now referring to FIG. 8 (in conjunction with FIG. 6) further details of the system digitizing and coupling the video signal to the S-100 bus may be seen. The phase 1 signal on line 104 is applied to a one shot 132 which acts as a vertical sync detector to reset a counter 134 on detection of the vertical sync signal in the composite video. In particular, the one shot 132 has a reset time equal to approximately one and one-half times the horizontal scan time so as to remain in the set condition except upon vertial retrace. The counter 134, on the other hand, also receives the horizontal sync signal on line 104 so that upon reset will count out 12 nonviewable lines of the forthcoming field (odd or even field) after which the clear signal to flip-flop 136 will be removed. The flip-flop 136 also receives the horizontal sync signal on line 104 as the clock input thereto, and is connected to provide a divide by two function to provide an output signal on line 138 indicative of an even scan line in the field (odd or even). The output of the divide by 12 divider 134 is also coupled to provide a start pulse which as shall subsequently be seen, is coupled to the computer to provide a start of field synchronization signal thereto. The vertical sync detector (one shot 132) is also coupled to a counter 140 coupled to provide a divide by 6 function to provide a ten cycle per second pulse rate on line 142, the function of which shall be subsequently described.

As each bottle reaches the target position, a target switch signal is received on line 144 which is coupled as shown in FIG. 8 to combine with the even signal on line 138 to provide the DFLSH signal on line 146. This "detect flash" signal does not actively drive the strobe but instead is coupled to pin 93 of the S-100 bus through latches 148 and tri-state buffers 150 (see FIG. 9). The output of latches 148 corresponding to DFLSH is referred to as the S flag, which is combined with the horizontal sync signal by flip-flop 152 to actually provide a signal on line 154 to trigger the strobe, and at the same time to reset the latch 156 which was initially set by the target signal, and to reset a corresponding latch 158, the function of which shall be subsequently described. Since it is a combination of the target signal and the "even" signal, i.e., even scan line signal which provides the DFLSH signal, and in essence is the combination of the DFLSH signal and the horizontal sync signal which actually drives the strobe, it may be seen that the device is actually triggered during the horizontal retrace of the first even scan line to end after the target switch signal is received. Since the strobe flash is very fast, the flash is complete before the next (odd) scan line starts, so that data on lines D0 through D3 may be clocked into the computer starting with the next odd scan line. The lines D0 through D3 of course, as well as the start signal STR, are coupled to the S-100 bus through the latches 148 and buffers 150. Thus the strobe may be fired during the horizontal retrace after any even scan line within either an even or odd field, after which all 240 digitized field lines will be read into memory through the S-100 bus.

Obviously, in general the 240 lines in any one field (odd or even) will be shifted vertically one line in comparison with the other field which in a six inch field of view translates to a vertical shift of approximately 0.025 inches. Also, since the strobe flash may occur after any even scan in any field, in general a first portion of the lines read in will come from one field, with the remainder coming from the next or opposite field. This of course could be avoided by either triggering the strobe only on vertical retrace (before which time the target bottle may move substantially in a high speed system), or data ingestion could be confined to fields of one type (odd or even) though this would require a camera of higher persistence (or specially constructed to always scan only one field) unless the strobe trigger was similarly delayed. It is believed however, that the scheme hereinbefore described wherein the strobe is triggered substantially immediately and data immediately read in, even though portions thereof may come from different fields, is preferable as it is more consistent with high speed operation and allows the use of a conventional video camera. Further, since label levels on bottles of a given type may vary substantially in elevation, the shift of plus or minus one line from field to field is very small in comparison thereto, and actually only represents 50 percent of one of the shift steps hereinbefore described used to counteract the differences in elevation between any library table and the target table. (In the embodiment described herein, data is always read in starting on an odd scan line, as the data is actually stored in memory as two four bit binary numbers making an eight bit byte of data, i.e., storage of two scan lines of data per memory address).

Now referring to FIG. 8, other aspects of the circuit shown therein will now be described. As previously described, the signal on line 144 is the target switch signal (MSCAN) provided by an appropriate sensor giving a trigger signal through an optoisolator when a bottle in the transport system reaches the target position. In addition however, equivalent signals may be derived from two other sources. In particular, a three position external switch 160 may be used to selectively ground lines 162 and 164, normally maintained in the high state by the pull-up resistors shown. Line 162, when pulled to the low state, enables NAND gate 166 so that the ten pulse per second signal on line 142 is coupled through the NAND gate 166 and NOR gate 168 to the flip-flop 158 which provides the XFLSH signal on line 154 for driving the strobe. In essence, this switch position may be used as a test position, i.e., by setting a bottle at the target position and moving switch 160 to the position to connect line 160 to the ground, the monitor 52 (see FIG. 1) will continually display the image of the bottle at the left portion thereof and the corresponding bar chart at the right side thereof as hereinbefore described. In that regard, perfect positioning of the bottle at the target position is not required, as the portion of each horizontal scan line devoted to bottle label digitization, as opposed to bar chart generation as indicated by the image on the monitor, is substantially wider than a bottle at the target position. On the other hand, when the switch 160 is in the position to couple line 164 to ground, NAND gate 170 is effectively enabled so that a library scan signal LSCAN will be coupled through NAND gate 170 and NOR gate 168 to trigger flip-flop 158 to also provide the XFLSH signal to drive the strobe on line 154 (the LSCAN signal, as shall subsequently be seen, is a computer generated signal used during the process of generating and storing the library table. Since the computer is generally tracking the raster scan, the LSCAN signal may be synchronized with each field so that the detect flash signal DFLSH on line 46 is synchronized with the start pulse to the computer STR on line 172).

Figure 9:
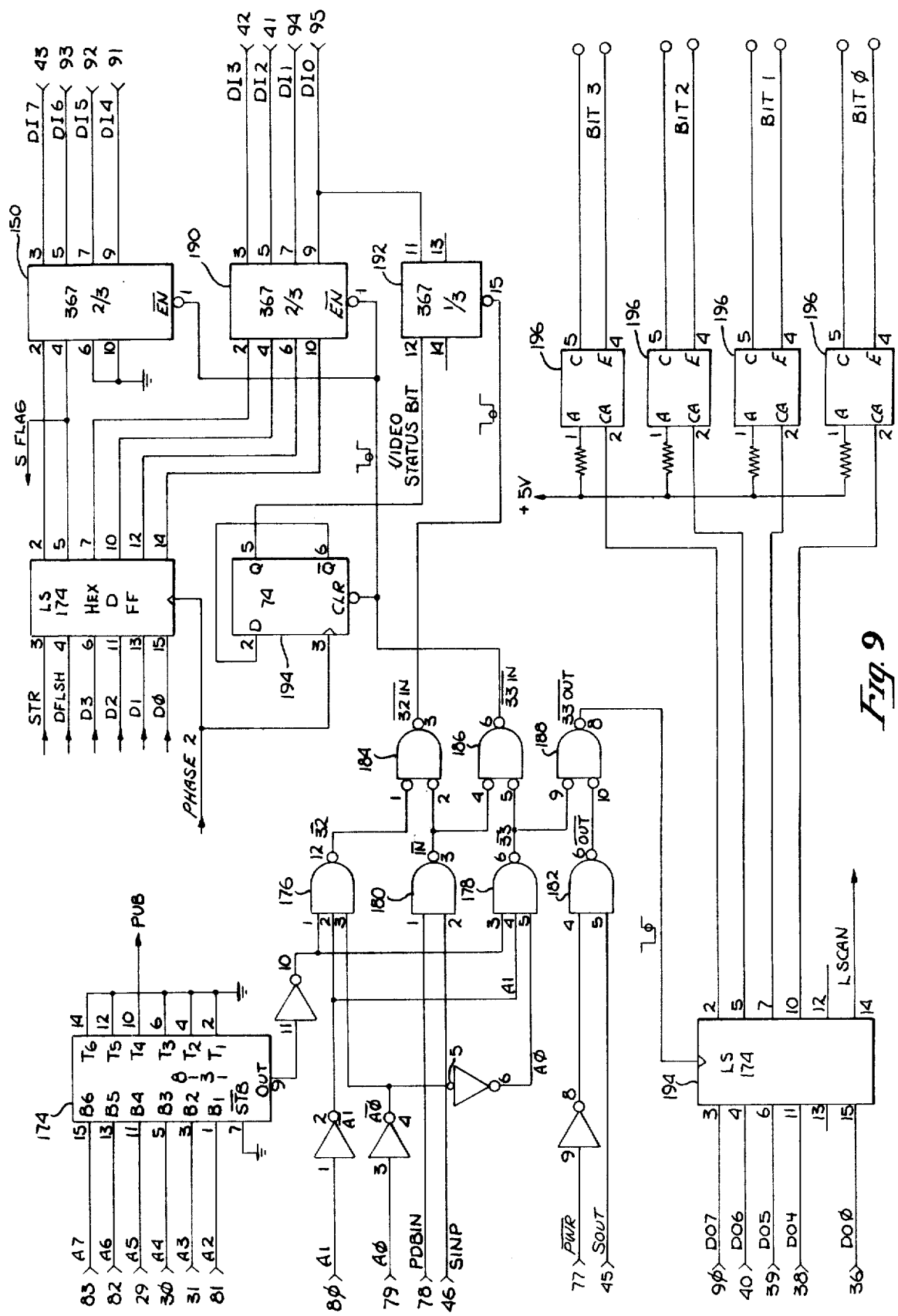
FIG. 9 is a circuit diagram for the I/O logic.

Now referring to FIG. 9, the circuit diagram for the input/output logic of the digitizer board may be seen. In this figure, various pin numbers are identified, as well as an identification given to the signal on the respective line. By way of example, the inputs to the six bit comparator 174 are identified as A2 through A7, representing the upper six bits of an 8 bit address. These signals are also identified by pin or terminal numbers 81, 31, 30, 29, 82 and 83 respectively. These terminal numbers and the address signals A2 through A7 are standard S-100 pinout designations, as may be seen by referring to any appropriate publication identifying S-100 bus connections. Similarly, the lower two significant bits, A0 and A1 of the eight bit address, are on S-100 plus terminals 79 and 80. The signals PDBIN, SINP, PWR and SOUT are also standard S-100 bus signals. PDBIN is the command/control signal out, which when high, requests data on the DI bus from the currently addressed memory or input/output device. SINP is a status output signal, which when high, indicates that the address bus contains the address of an input device and the input data should be placed on the data bus when PDBIN is active. PWR is the command/control signal out which, when low, signifies the presence of valid data on the data out bus for memory write or input/output device output. SOUT is a status output signal which, when high, indicates that the address bus contains the address of an output device and the data bus will contain the output data when PWR is active. Also shown in FIG. 9 are the connections for DO0, DO4 through DO7 and DI0 through DI7, the DO signals representing data output signals and the DI signals representing data input signals. (The words input and output in this convention relate to computer signals, the output signals DO0 and DO4 through DO7 representing computer output signals or input signals to the I/O logic of FIG. 9, and the data input signals DI0 through DI7 representing output signals of the circuit of FIG. 9 to form input signals for the computer.)

The six bit comparator 174, as connected, recognizes decimal addresses 32 through 35, the address lines A0 and A1 being isolated and used for further address refinement. In particular, NAND gates 176 and 178 recognize addresses 32 and 33, their outputs going low anytime the low order eight address bus lines contain a count of 32 or 33 respectively. Inasmuch as the complete address bus is 16 lines or 16 bits, the decoded outputs will be active in each of 256 segments of the total 64 K address range. Any or all of these segments may be addressed during program execution. However, for an I/O port access, only eight bits of address are used and the address is duplicated on the upper and lower halves of the address bus. This is done to allow better distribution of address bus loading in systems with many I/O devices.

The two status signals, SINP and SOUT define when the address bus contains I/O addresses. SINP indicates an input address and SOUT indicates an output address. In addition, two processor signals define when data is valid, specifically PDBIN indicates the input should drive the data inlines and PWR indicates the data is valid on the data outlines to an outport. NAND gates 180 and 182 resolve the associated function pairs and generate the signals IN and OUT. These signals are general and occur for any input or output instruction execution regardless of address. NAND gates 184, 186 and 188 resolve the specific control signals for ports 32IN, 33IN and 33OUT.

The hex flip-flop 148 previously mentioned, is clocked just before the video down count is commenced by the leading edge of phase 2. The outputs D0 through D3 are the accumulated video count for the current TV scan as hereinbefore described. DFLSH indicates that the strobe light will flash at the next horizontal sync time. At the output side, it is labeled SFLAG and will indicate to the processor that the next data byte will be the first valid value for making up a target table. STR indicates the start of a TV field and at the output side is labeled FFLAG and will allow the processor to synchronize a line count to the TV camera. For synchronized scans (10PPS or LSCAN as discussed with respect to FIG. 8) the S and F flags occur in the same byte.

Hex bus drivers 150, 190 and 192 are used by the input ports to drive the data lines. These devices are divided into quad and dual sets, each with its own control input. The two quad sets 150 and 190 are used to drive video words onto the data input bus. 33IN is a control signal enabling the drivers while it is low. 33IN is also connected to the CLR terminal of flip-flop 194. This flip-flop is clocked set by phase 2 when a new byte is loaded into the hex D flip-flop 148. Its Q output is used as an active low status bit which is driven onto data input line DI0 when 32IN is low. The status bit becomes active when a new data byte is available and is cleared when the data byte is read in by the processor. Inport 32 is a shared status port with other bits available for use by other system elements when responding to an inport 32 read by the processor.

A second hex D flip-flop 194 is used to register the data for outport 33. DO0 is the LSCAN signal and DO4 through DO7 are the four bit gate number for the last correlation (DO3 is a spare). The gate number bits are isolated by optoisolators 196 to provide an isolated four bit binary number to the transport system for decoding into as many as 16 gate selections to sort up to 16 different kinds of bottles. Obviously, while the system is capable of sorting even greater number of bottles, 16 is more than adequate for substantially all applications as most mechanical bottle handling systems are limited to some lesser number. Further, even though the system has the capability of storing up to 63 library tables, the preferred manner of using the system envisions that 2 views of each type of bottle to be recognized be stored in the library, specifically a "zero degree" view and a "90 degree" view. Thus the 63 library table capacity in such event would be reduced to a 31 bottle capacity, and may be further reduced if additional views of any bottles are used.

Referring now momentarily to FIG. 1 again, it may be seen that the correlator board 56 as well as the central processing unit 50 and random access memory 54 all communicate on the S-100 bus. Since the denominator of the correlation coefficient fraction is the larger total count from the total count values for the target table and the library table, the total counts are computed by summing all scan line counts for a table. These counts are generated by the computer each time a bottle view is digitized, as obviously all required information is available over the S-100 bus. The overlap count however, is provided by the overlap count logic on the correlator board 56 which provides the highest overlap count of the 16 passes. This highest count is then transferred over the S-100 bus to the processor which then divides the overlap count by the larger total count to provide the correlation coefficient. This process is repeated for all 63 library tables with the highest of the 63 correlation coefficients determining the "selected" bottle. Obviously, if two views of the same type of bottle had been stored as separate library tables, the computer will identify either of these library tables which has been selected as selecting that bottle, or more specifically as selecting the control for the desired outlet conveyor for that bottle. As previously described, the output representing the selected bottle will be provided on the output lines D04 through D07 (see FIG. 9) on the S-100 bus for decoding and control of the transport system. In the transport system described herein with respect to the preferred embodiment, a bottle is identified at the target position, though release thereof will come sometime thereafter depending upon the identification of the bottle and the position of the respective outlet conveyor. Accordingly, either the processor may be programmed to delay the output identifying the bottle a given number of target switch signals MSCAN (the preferred method), or alternatively, some appropriate form of delay may be provided at that outlet gate control.

In a low speed system, the function of the correlator board 56 could be done under program control by the processor 50. However, because of the number of calculations which must be undertaken, the preferred embodiment uses the correlator board to provide these calculations at an extremely high speed so as to allow high speed operation of the bottle sorter. In particular, the prototype camera-electronics system built in accordance with this disclosure is capable of sorting bottles at the rate of 600 per minute, and with only minor modifications could go to 1200 bottles per minute if a mechanical bottle handling system could be fabricated to operate at such speeds.

It is probably best to disclose in block diagram form the overlap count logic of the correlator board and provide a general description thereof, and at the same time present the detailed circuits thereof, tying in the general functional blocks and the block diagram description with the detailed circuits. Thus, FIGS. 10 through 13 provide general block diagrams of the organization of the correlator, whereas FIGS. 14 through 17 present the detailed circuits thereof.

Figure 10:
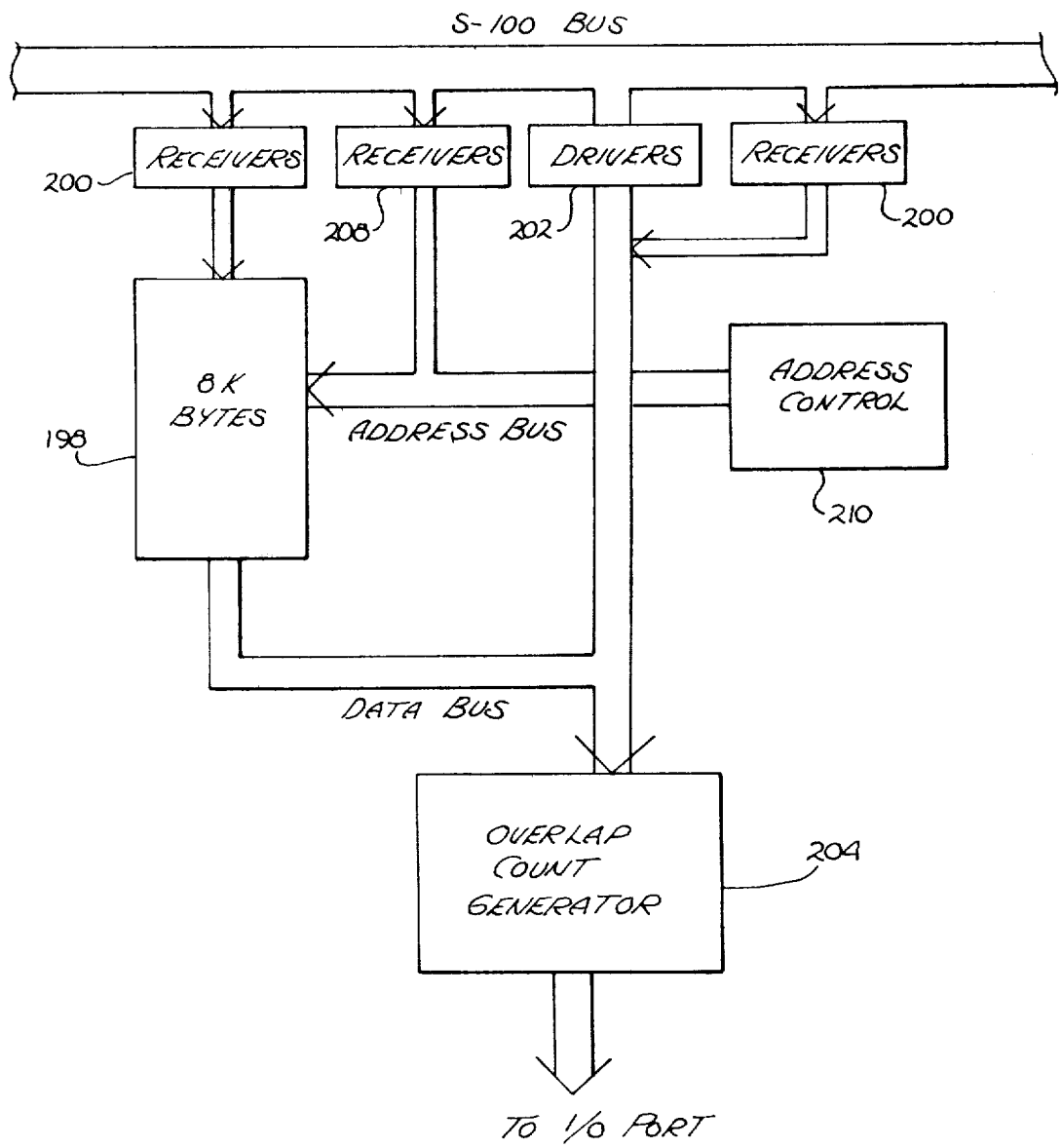
FIG. 10 is a block diagram of the correlator.
Figure 17B:
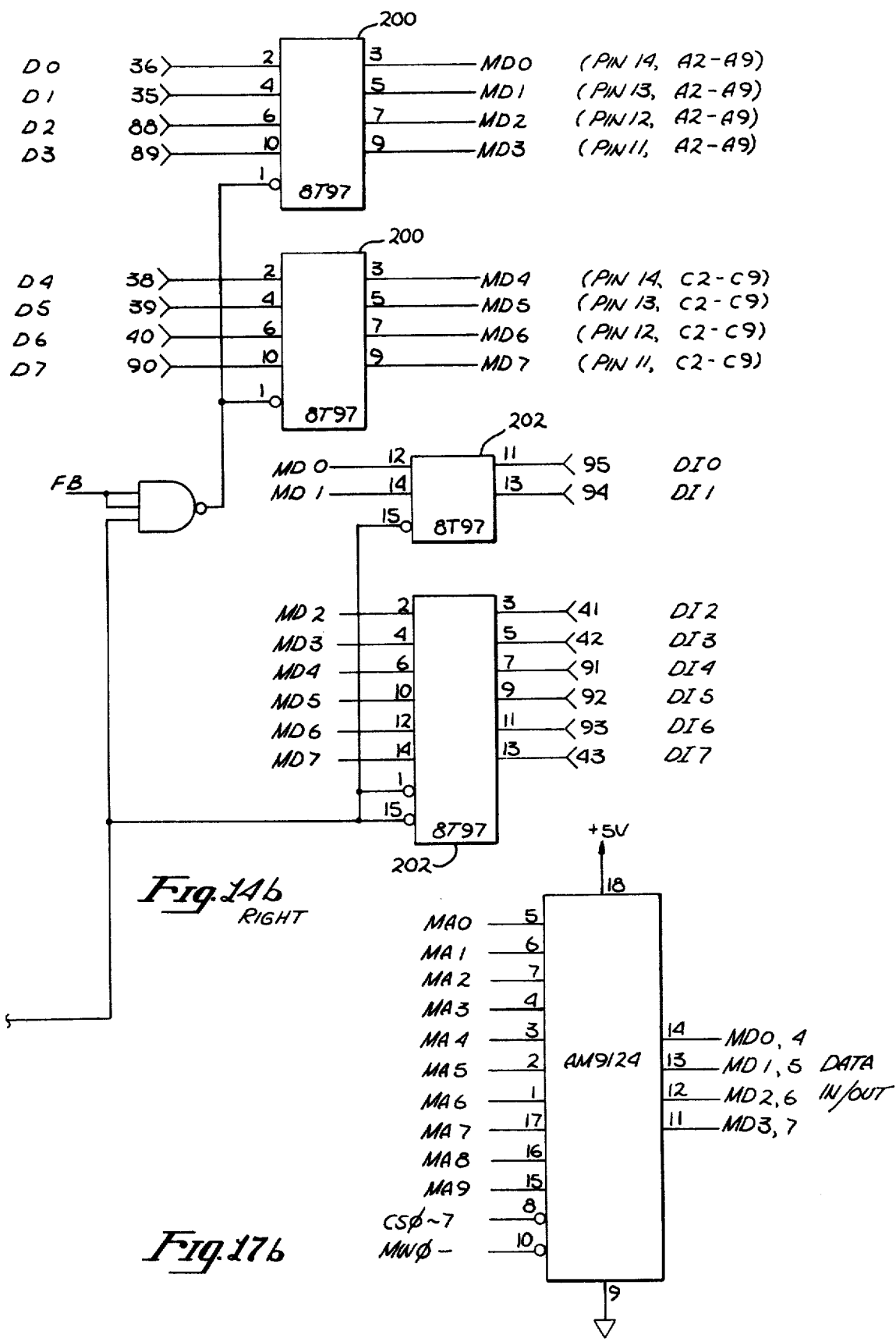
FIG. 17b is a diagram illustrating a typical library table memory device.
Figure 17A:
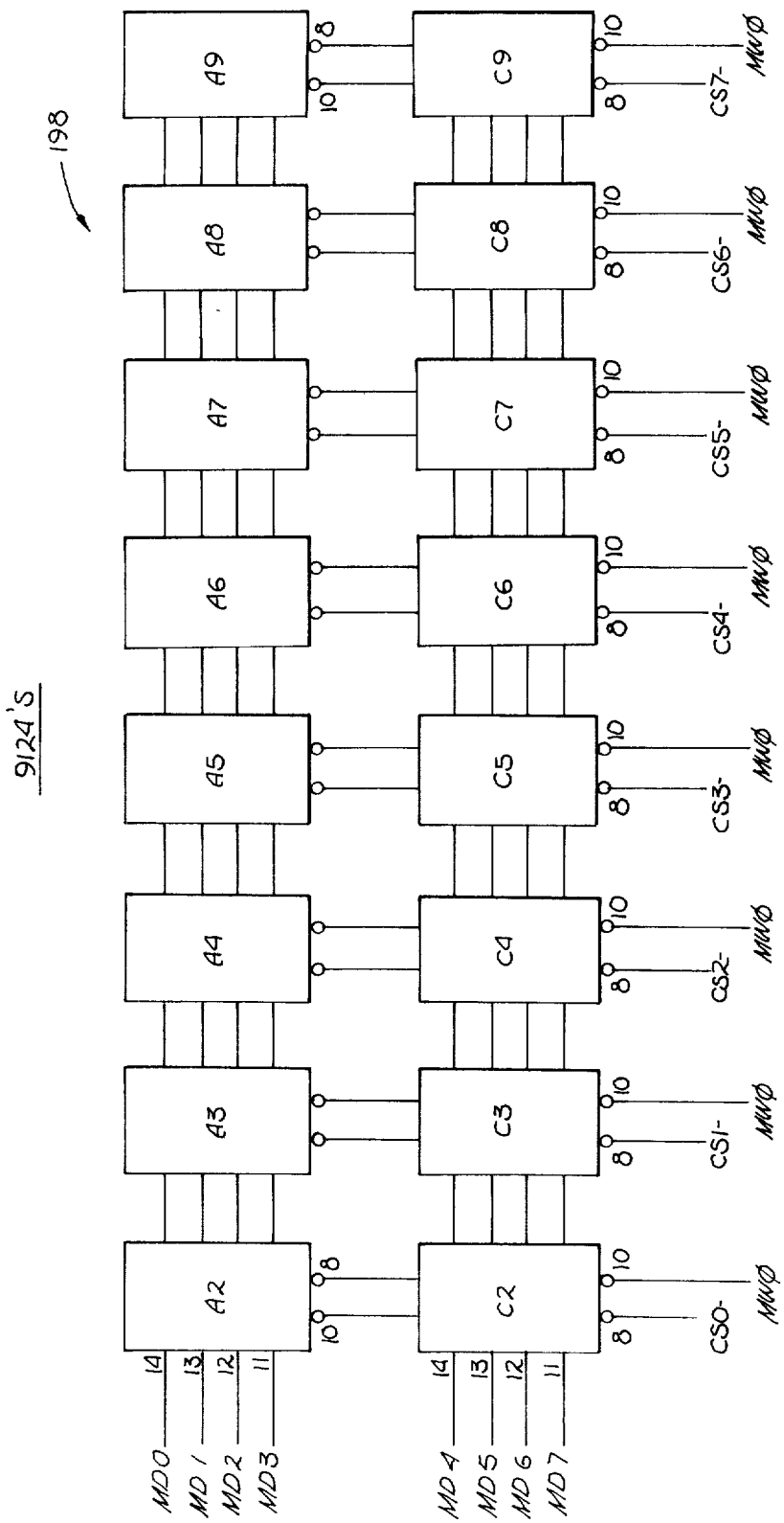
FIG. 17a is a block diagram illustrating the organization of the library table memory.

In FIG. 10 a general block diagram of the correlator board may be seen. An 8 K by 8 random access memory 198 is coupled to the S-100 bus through receivers 200 and drivers 202 so as to be able to receive data from and present data to the bus. In the preferred embodiment the individual memory devices are AM9124s shown typically in FIG. 17. Also shown in FIG. 17 is a general interconnection of the AM9124s to provide an 8 K byte storage capacity. The receivers 200, as well as the drivers 202, may be seen in FIG. 17. The memory is also coupled to the overlap count generator 204 (in FIG. 10) to present data thereto for calculation of an overlap count. The output of the overlap counter in turn is coupled to two I/O ports used to transfer each overlap count through a standard port inerface board. The overlap count generator 204 may also receive data directly from the S-100 bus through receivers 200. Memory address is provided on the S-100 bus through receivers 208 controlled by an address control 210. The 8 K byte memory 198 provides for storage of 64 tables of 128 bytes each, each table containing 240 scan counts of 4 bits each. The scan counts are packed 2 per byte and therefore require 120 bytes for each table. The remaining 8 bytes of each table hold the total count, bottle number and gate number. Also of course, there is additional random access memory for general use by the processor which is not shown in FIG. 10.

The general memory organization of memory 198 of FIG. 10 may be seen in block diagram form in FIG. 11 and in the detailed circuits of FIGS. 14 through 17. The S-100 bus provides 17 address lines, 8 data in lines, 8 data out lines and several control functions. In addition to the 8 K memory on the correlator board, there are 7 other 8 K byte memories located elsewhere of similar organization. A0 through A12 address one of the 8 K memory locations in each 8 K memory (decoding being onchip) with A13 through A15 being coupled to decoder 212 to provide a fully decoded one of 8 output. The decoder 212 on each memory board is strapped differently so that only one 8 K memory is selectable at any time, i.e. address bits A13 through A15 forming the 8 K memory select bits. It may be seen also from FIG. 14 that address bits A10 through A12 provide the chip select within an 8 K memory, whereas memory address bits MA0 through MA9 select one of the 1,024 four bit words in each row of the selected memory. There is also provided an 8 bit data bus MD0 through MD7 which provides the data path for either reading or writing the memory based upon a write control line to each row. The data bus is taken to the overlap count generator and the address bus can be driven from the address control section 210 of FIG. 10. The function FB prevents simultaneous access to the memory, i.e., when FB equals one, only the Z80 processor can communicate with the memory, whereas when FB equals zero, only the internal functions can communicate with the memory.

FIG. 12 (as well as FIGS. 15 and 16) illustrate the elements of the address control section. Three counters are provided, specifically the scan counter 214 (K0 through K7), the precess counter 216 (P0 through P3) and the table counter 218 (K8 through K15). An 8 bit adder 220 is provided which allows addition of the precess offset (previously described) to the scan counter. Selectors 222 and 224 are provided to select (a), the unmodified scan count or the precessed scan count; and (b) select the target table (table 0) or the library tables. These selectors drive the memory address bus (MA00 through MA12).

Table and precess selection is controlled by the signals K0 and P3. In order to compare individual scan lines, the scan line count from both a target and library table must be transmitted to the overlap count generator. This is accomplished by two accesses to the table memory. On one cycle (K0 equals 0) a scan count from one of the tables is addressed for transmission to the overlap count generator. On the other cycle (K0 equals 1) a scan count from the precess table is transmitted to the overlap count generator. The pass number shown in the table below is equal to the value of the precess counter 216. On the first eight passes (P3 equals 0), the precess count is added to the library tables, and on the second eight passes (P3 equals 1) the precess count is added to the target table. The following table illustrates the selection of tables and precess additions as a function of K0 and P3.

| P3 | K0 | |
|---|---|---|
| 0 | 0 | target table unmodified |
| 0 | 1 | library table + precess count |
| 1 | 0 | library table unmodified |
| 1 | 1 | target table + precess count |

The scan line address is generated by K1 through K7. Scan lines are addressed in sequence until the output of the adder 220 reaches 120. At this time operations in the overlap count generator are completed for that pass and the precess count of the precess counter 216 is incremented by one. After 16 passes are completed, the precess counter resets to zero and one is added to the table counter (K8 through K15). At the same time the overlap count generator transmits a selected overlap count to the Z80. The process is then repeated for the next library table and continues automatically through library table number 63 at which time the process is halted and will not resume until again initiated by the Z80 program.

Two control flip-flops 226 (FA) and 228 (FB) are used to provide system timing. In addition, three external signals provide (i) a 4 mHz clock XCL, (ii) a reset signal XRS, and (iii) a start signal XST. Reset signal XRS sets FB and resets counter stages K7 through K15. FB, when set, will in turn set FA and reset K0 through K7, P0 through P3, AC0 through AC11 and OR0 through OR11. This condition remains until the receipt of the first XST which resets FB. This allows K0 through K7 to start counting and initiates 16 passes which compute for each pass an overlap count between table 0 (the taget table) and table one (the first library table). At the end of the 16th pass the load port signal LDP will transfer the contents of the overlap count register to two 8 bit output ports. At the same time FB is set, which inhibits further processing. Once the Z80 has taken the overlap count and accessed any information from the tables it may require, it reissues a second XST signal. This series continues until the target table has been compared with all 63 library tables. Thus, in summary, the start pulse XST resets FB which releases the counter K0 through K7. FA is set on the falling edge of the first K0 pulse. FA is used to generate ACL (the accumulator clock) which adds partial accumulated counts to AC0 through AC11. Gate 230 (FIG. 12) detects an output of adder 220 of 120, and at the end of this cycle FB is turned on.

The last ACL clock at count 120 adds to the accumulator the last partial count generated during the first half of count 120. Following this, the accumulator and overlap count are compared and if the accumulator is larger, its value is entered into the overlap counter with the leading edge of FA. When the count from the adder reaches 124 the function PCL is generated. PCL is used to reset K0 through K7, add one to the precess counter and reset the accumulator. This initiates the second pass. With respect to the relationship of K0 and ACL, during count zero, the leading edge of K0 loads the unmodified register RB0 through RB7. On the trailing edge of K0 the precessed register RA0 through RA7 is loaded. One clock pulse (250 nanoseconds later) the first ACL clock edge loads the first partial count into the accumulator.

The timing for the last of the 16 passes is similar to the timing for the first passes with a few exceptions. At the start, the adder count shows the precessed value of 7 since the precess counter is at the count of 15. At the end of the pass LDT (the carry out function of the precess counter) will cause the contents of the overlap counter to be transferred to the two 8 bit I/O ports. LDP also enables FB to be set on the trailing edge of PCL. Once FB is set the process is halted.

The sixty-third XST will initiate the last sequence of 16 passes. The table count represented by K8 through K15 will be advanced to the count of 64 at the leading edge of LDP. Output K14 is taken to the high order bit of the second IO port and indicates to the computer that all 63 overlap counts have been generated.

Figure 13:
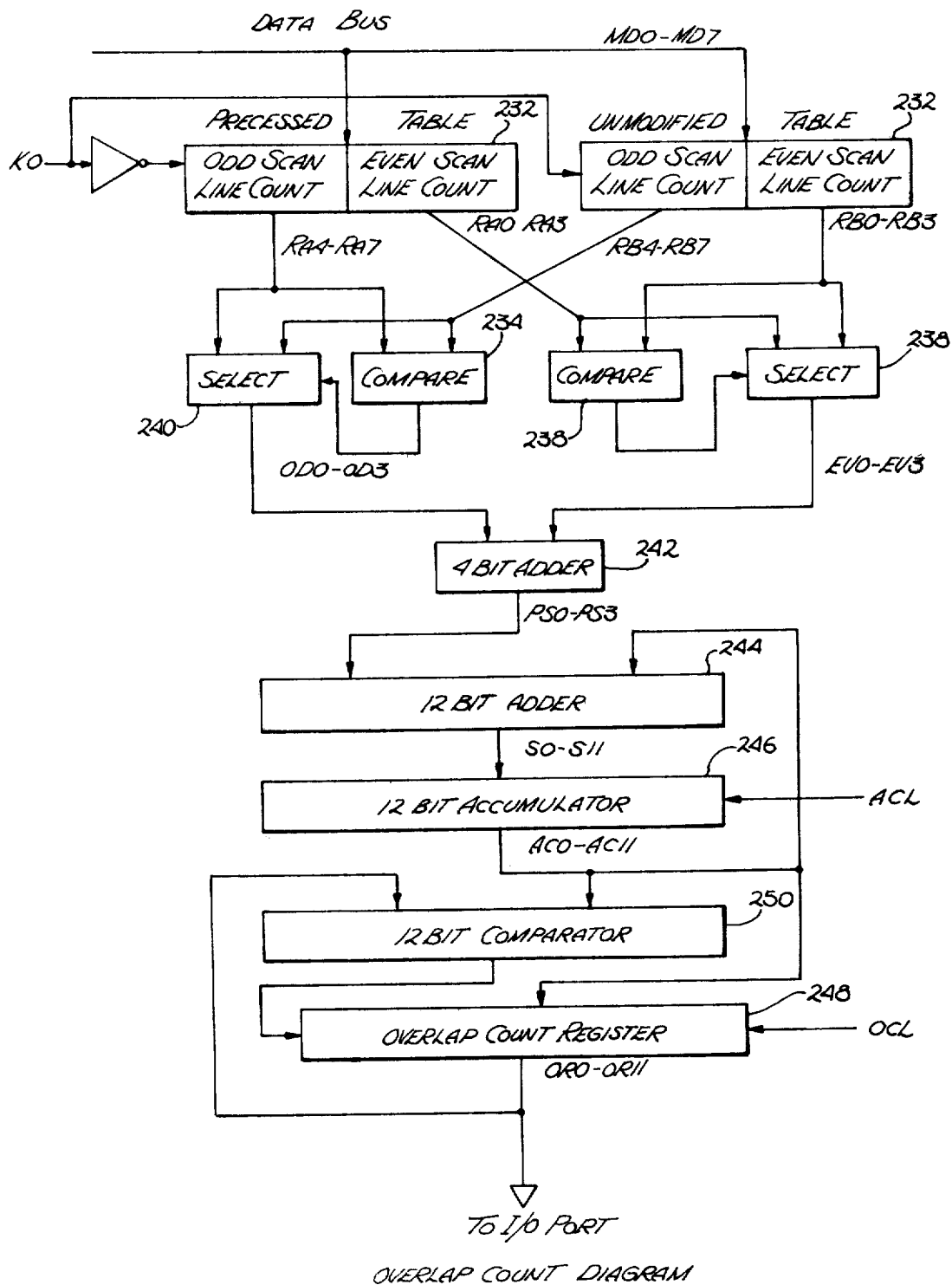
FIG. 13 is a block diagram of the correlator.
Figure 14A:
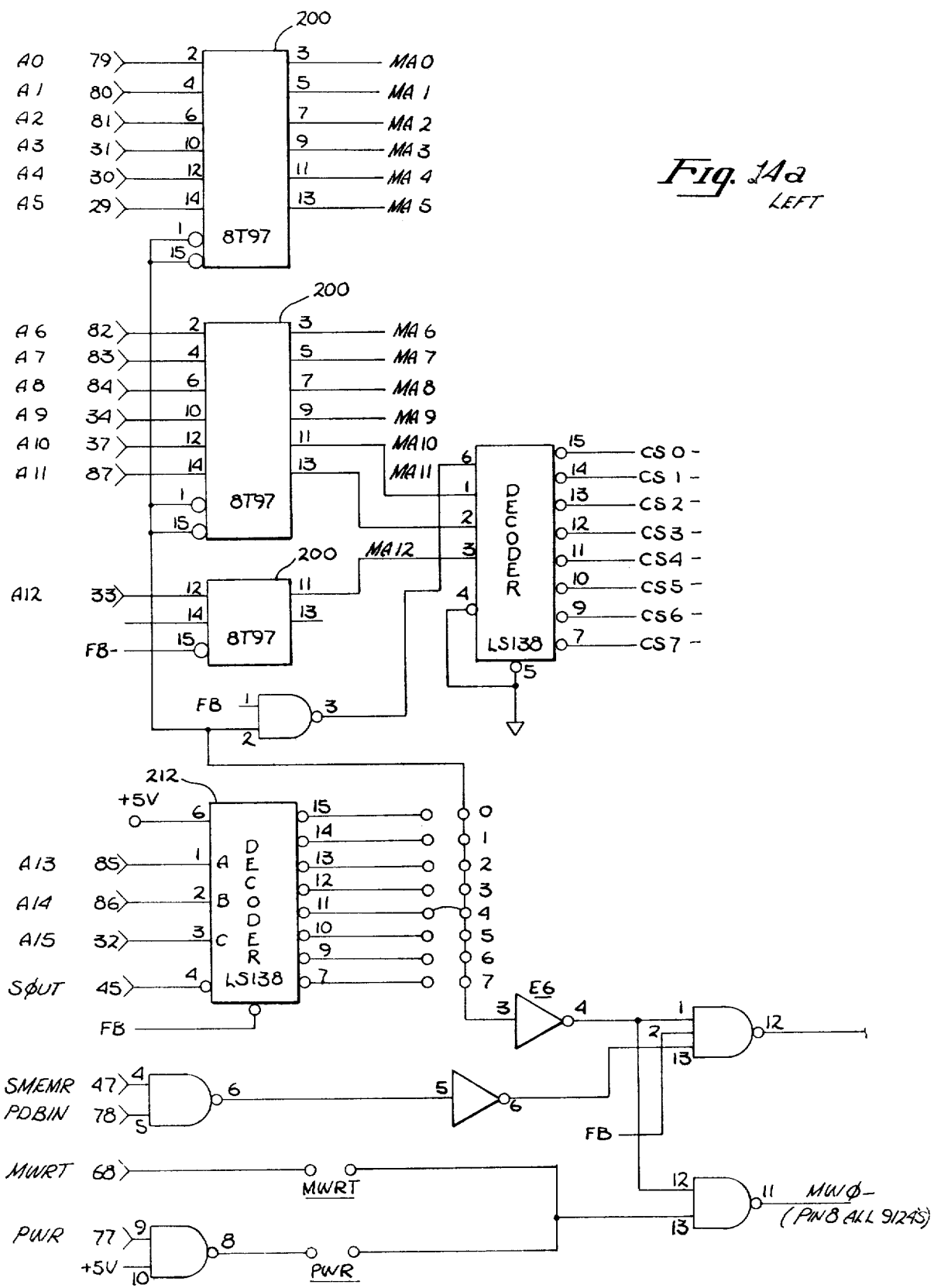
FIGS. 14a and b are left and right circuit diagrams, which together comprise part of the correlator logic.
Figure 15A:
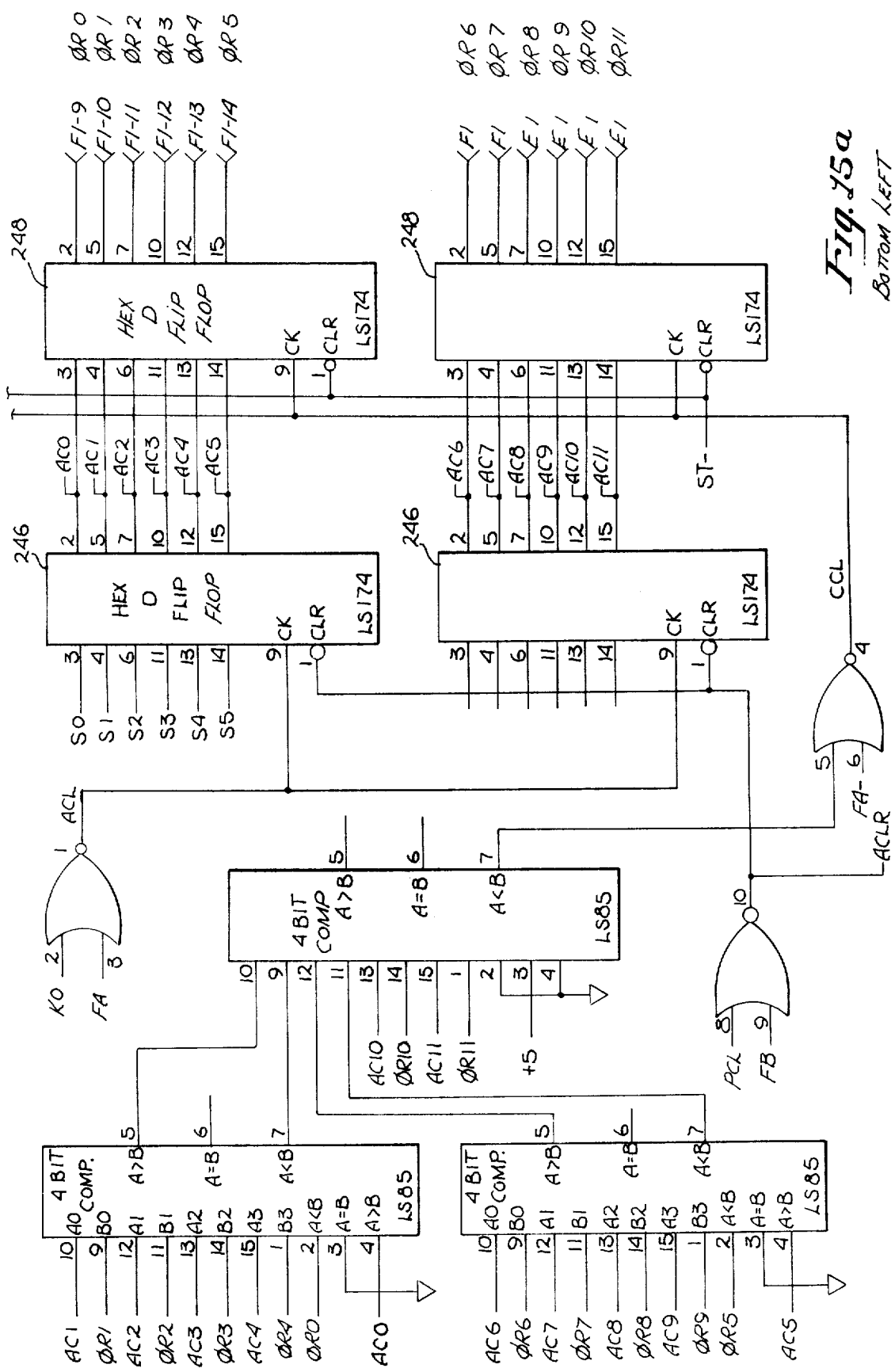

The block diagram of FIG. 13 and the detailed circuit of FIG. 15 illustrates the elements of the overlap count generator. Two 8 bit table registers 232 are provided, one for holding a memory word from the table being precessed and the other for holding a memory word from the unmodified table, each memory word, of course, containing two 4 bit scan line counts.

These registers are coupled to two 4 bit comparitors 234 and 236, one of which compares the magnitude of the two even scan line counts (i.e., comparitor 236) and one to compare the two odd scan line counts (i.e., comparitor 234). Comparitor 236 controls a selector 238 and comparitor 234 controls a selector 240, each of the selectors being used to select the lower counts. The lower count of the two even scan line counts and the lower count of the two odd scan line counts are transferred to a four bit adder 242 where a partial accumulated count is generated.

During a single pass between the target table and the library table, as many as 120 partial counts may be generated. These partial counts are accumulated by the 12 bit adder 244 as signals S0 through S11, and the 12 bit accumulator 246 as signals AC0 through AC11. At the end of each pass, the value held by the accumulator 246 is compared to the value held in the overlap count register 248 by a 12 bit comparator 250. If the accumulator value is higher it will be transferred to the overlap count register 248. At the start of each pass the accumulator 246 is reset to 0. At the end of a full 16 pass sequence the contents of the overlap count register 248 are transferred to the Z80 via the two I/O ports and then reset to zero prior to the start of the next sequence.

Figure 25:
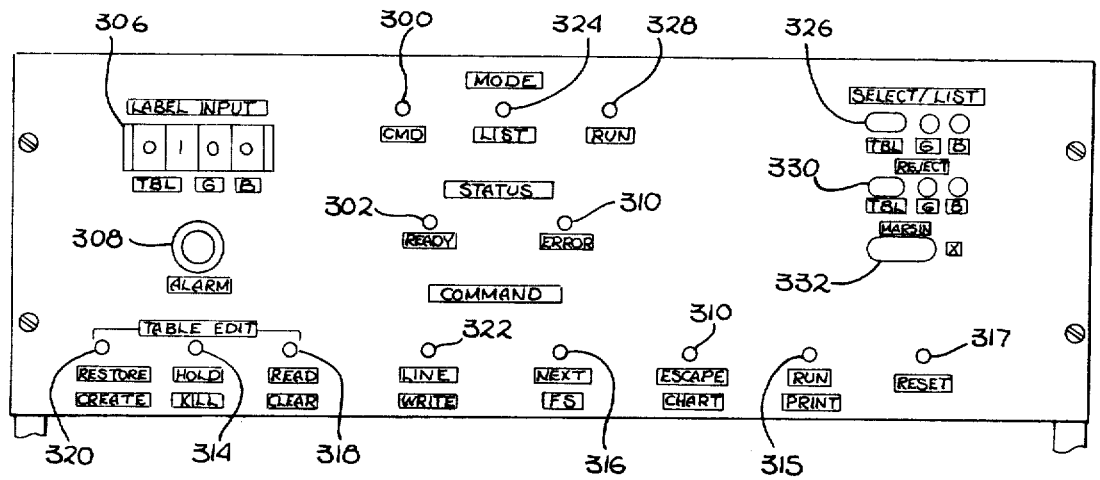
FIG. 25 is a drawing of the front panel of the system.

Having now described the operation of the system once the library tables have been created, the manner of programming the system will now be described. In the preferred embodiment, the electronics and computer are packaged in a standard chassis which may have its separate enclosure or be provided as a rack mount. A front panel for a typical rack mount may appear as shown in FIG. 25. The front panel is characterized by a plurality of switches, lights and indicators for both monitoring and controlling the system. To initiate programming of the system, power is turned on to all system components, specifically the computer, camera and digitizing circuitry. Also, it is most convenient to use the video monitor 52 (FIG. 1) so as to be able to view pictorally that which the system is digitizing and storing. On power up in a production system, the system will automatically enter the program PRCOG, though in the system in accordance with the software attached hereto as an appendex, PRCOG is entered by examining address A000H and pressing the RUN switch 315. Under these conditions the CMD mode light 300 will come on, indicating that the system is in the COMMAND mode, as will the ready status light 302. At the same time, under program control the system will proceed to clear the table memory so that unused tables will be cleared rather than having a random content. This insures that there is no random data in the memory which could confuse the program.

Figure 18:
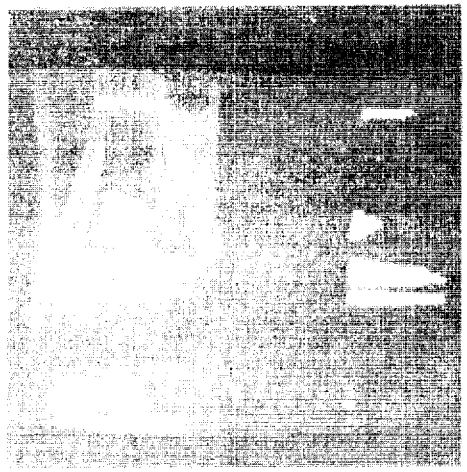
FIGS. 18, 19 and 20 are reproductions of the monitor image obtained, utilizing one liter 7UP, Diet 7UP and Sprite bottles respectively.
Figure 19:
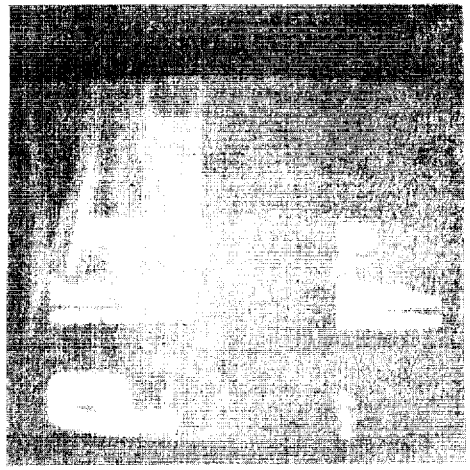
Figure 20:
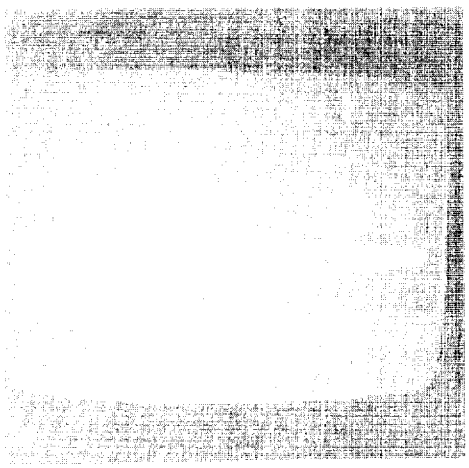

The switch 304 corresponding to the EXT switch in the lower left hand portion of FIG. 8 is then set to the ten PPS position, which as previously explained, will cause the strobe to flash at a continuous rate of ten pulses per second. At this point, assuming the video camera is reasonably well positioned, the monitor 52 (FIG. 1) should show the bottle at the target position at the left of the screen and a bar chart at the right of the screen as hereinbefore explained. Preferably an adjustable intensity strobe is used so that the strobe intensity, camera position, aperture and focus can be adjusted so that a clear bottle image of appropriate size and contrast is obtained in the left portion of the screen. FIGS. 18, 19 and 20 provide examples of the monitor display for a one liter 7UP bottle, a one liter diet 7UP bottle, and a one liter Sprite bottle at the target position, respectively. Note that immediately to the right of each of the bottle images are the corresponding bar charts for the digitized label. Note particularly that the number of light to dark transitions in scanning the words "money back bottle" on the 7UP bottles generally exceeds the maximum count of 15 in the preferred embodiment, whereas other portions of the label, such as the scanning of the upper portion of the "P" in the 7UP bottles only gives one, or at least a very few transitions. Also as shown in these figures, portions of the bottle out of the region of the label in general will create no bar chart (i.e., a chart of zero height in these regions) indicating that no light to dark transitions were sensed. Once the camera and strobe are appropriately adjusted, the digitizer switch is turned from the 10 PPS position to the LSCAN position to ready the system for creation of the library tables.

All PRGOC commands are given using the miniature toggle switches along the lower portion of the front panel. It will be noted, referring to FIG. 25, that there is a double row of labels below both of the switches. By way of example, the NEXT switch is also labeled F2 in the lower row. This means that the NEXT switch also serves the purpose of enabling the second function for the other switches. (In most cases this provides protection from an operator accidentally doing disastrous things to the table memory by making the second function only accessible by first depressing the NEXT switch.)

All commands which can affect table memory are grouped to the left of the front panel under the title "TABLE EDIT". The first of these commands is the CREATE command which is used to generate library tables. This command also requires use of the four LABEL INPUT switches 306 at the upper left of the front panel. These switches allow the table to be identified with table number (the left two digits), gate number (the third digit), and bottle number (the fourth digit). The table number determines the table location in the table memory, whereas the gate number determines the machine lane to which a bottle, once identified as corresponding to that table, will be directed, i.e., which output conveyor it will be directed to. In general, one should normally record more than one view of each bottle, typically preferably a straight on shot at the label and a 90 degree shot, i.e., with the bottle rotated 90 degrees from the first position. Thus the bottle number also distinguishes log entries for tables which have the same gate number, i.e., either different views of the same bottle, or different views of one or more other bottles also in the event more than one bottle type is to be directed to a particular outlet conveyor.

To make a table, one should have a log sheet for logging the table, gate and bottle numbers as the library tables are created in order to have a convenient reference to this information, as is at least partially predetermined by knowledge of the gate and bottle combinations desired to sort the incoming mix of bottles and direct the sorted bottles to the appropriate outlet conveyors. Once the log is made, the LABEL INPUT switches are set to agree with the first log entry. The corresponding target bottle is set in the target position, the NEXT switch is depressed, and while held down, the CREATE switch is depressed. This will cause the strobe light to flash 16 times, with the 16 images being digitized, averaged and loaded into the table memory in the corresponding position for that log entry. At the same time the bottle number and gate number as set by the LABEL input switches is stored, and total count is computed and also stored as a trailer to the table. (Each table memory is 128 bytes, whereas only 120 bytes are required to store the 240 digitized scan lines of any one table.) If there is already an active table with the same table number, the system will create a beeping sound through the alarm 308 on the front panel and the active table will not be overridden. If, on the other hand, it is intended to override that location, the next switch may be again depressed and the command will be completed, i.e., the table will be overridden. However, if the initial aborted attempt to override the active table was recognized as a mistake after the alarm sounded, the attempt to override the table can be aborted by depressing the ESCAPE switch to return the system status to READY without completing the table creation.

Various errors will result in a beep and a red ERROR light, specifically light 310 on the front panel of FIG. 25. These represent conditions which the operator must be forced to consider in order to correct the log. This condition is called ERROR TRAP, and can only be exited with the ESCAPE switch 310. These label input errors occur when one attempts to put in table numbers which are not allowed. By way of example, setting the table number equal to zero is not allowed, as table zero is the target table for the RUN mode and cannot be used as a library table storage location. Similarly, a target table number exceeding 63 is not allowed in this embodiment, as the table memory does not extend past table 63. In addition, while the switches 306 admit to gate numbers and bottle numbers of zero, the system software does not, so that any attempt to use the gate number of zero or bottle number of zero will also result in a beep as a label input error.

The KILL command of switch 314 removes a specific table from the library by filling its portion of the table memory with zeros. Consequently, it only makes use of the table number part of the label input switches so that the gate number and bottle number inputs are ignored. The KILL command is simply executed by depressing the NEXT switch 316 and the KILL switch 314. The CLEAR command is similar, though it deletes the entire library by filling the entire table memory with zeros and is executed by depressing the NEXT switch 316 and the CLEAR switch 318.

The HOLD command is used to remove a library table from the correlation process during the RUN mode, i.e., a table on HOLD is ignored in the RUN mode. The content of the table is not disturbed however, and can be removed from HOLD at a later time. The HOLD command is executed by setting the table number switches to the table to be put on HOLD and then depressing the HOLD switch 314 (note in this instance that the NEXT switch 316 is not depressed so that the upper function of 314 is executed). If there is no such table in the library or it is already on hold, an error trap will be entered. In such event one should double check the log after which the condition can be exited by depressing the ESCAPE switch 312 (the upper function of switch 312). The RESTORE command is used to return a table on hold to active correlation. Again, the table number switches are set to the table on hold which is to be restored and the RESTORE switch 320 depressed. Again, if there is no such table or it is already active, an error trap will be entered, indicating that the log should be checked with the condition being exited by depressing the ESCAPE switch 312.

A LIST command is provided for two purposes. Specifically, the listing of the library tables for verifying the log, and to determine the reason for an error trap. For verifying the log, the table number switches are set to the first table to be listed and the LIST switch 322 is depressed. The mode will change to LIST (i.e., light 324 will come on and the table label data will be displayed on the select/list alphanumeric character display 326 on the front panel). The listing may be advanced through the library by successive depressions of the NEXT switch, with the listing procedure being terminated either by pressing the ESCAPE switch or automatically after table 63 is listed. At any time an inactive table is encountered, including time of entry, the beep alarm will be sounded. If the table was never created or has been killed, the gate and bottle display portion of the display 326 will show "00". If the table is on HOLD, the gate and bottle display portion will show normal numbers.

A RUN command is used to enter the operating mode in which bottles are identified, and is entered by pressing the RUN switch which will cause the mode status lights to change to illuminate the RUN light 328. If the bottle handling machine is not active, the READY light 302 will be steadily on, indicating that PRCOG is waiting for target switch signals. If the handling machine is on, i.e., target switch signals are being received, or is then turned on, the READY light will flicker, indicating correlations are being done. The result of each correlation is three fold. First, the label of the table with the highest correlation factor is shown in the SELECT/LIST display 326, with the gate number portion of the information being sent to the bottle handling machine for gate control. Second, the label of the table with the closest correlation factor, but with a different gate number, is shown in the REJECT display 330. Note that this table is not necessarily the one with the next highest correlation factor, in that the table with the next highest correlation factor may be a different view of the same bottle, or even another bottle type having the same gate number if more than one type of bottle is to be directed to the same outlet conveyor. Thus the table data displayed in the REJECT display is the one which comes closest to making an error by directing the target bottle to the wrong lane. Third, the difference between the correlation factors for the select and reject tables is displayed in the MARGIN display 332, displayed as a decimal percent. The margin is a useful number in that the larger the margin, presumably the greater the certainty in the accuracy of the identification. Continuous correlations of a stationary target may also be done if desired, to evaluate the effects of bottle rotation, etc., by setting a bottle in the target position with the handling machine off, and setting the EXT switch to the 10 PPS position for so long as continuous correlations are desired. For a single correlation, the system is put in the run mode, the digitizer set to LSCAN and the NEXT switch momentarily depressed. The correlation will be done on the release of the switch, in this instance the target scan being synchronized, i.e., strobe at the top of the field.

In the embodiment disclosed herein, the library tables are stored in random access memory and accordingly will be lost on a power down condition unless sustained by a battery back-up system. The advantage of this, of course, is that the system is "self teaching" in that any library tables desired can be readily created by the user as opposed to requiring a predetermination at the time of manufacture of the equipment. Obviously however, predetermined tables could be stored in read-only memory which would avoid loss of the tables on power down. In any event, in the embodiment disclosed herein, provisions are made for WRITE library and READ library tape commands. The WRITE command makes a cassette tape record of the library tables for nonvolatile storage and does not effect the contents of the library tables when doing so. The procedure is to load the cassette into the tape recorder and connect the recorder to the rear panel of the computer. The controls of the tape recorder are set for record and pause. The NEXT and WRITE switches 316 and 322 are depressed and the pause quickly released so that tape motion is initiated. An automatic leader will be written and a beep will sound when the recording is done. To read the tape back into the table memory, the recorder of course is in the playback position, and with the leader playing the NEXT and READ switches 316 and 318 are depressed. A beep sound will be provided when the read operation is complete. In both the READ and WRITE functions, the MARGIN display 322 will indicate activity is occuring during the process. Finally, the system is provided with a capability of displaying bar charts corresponding to the stored library tables (as opposed to the target bottle) and for printing out these bar charts, if desired. The display function displays 80 bars from a data table on the monitor. This is achieved by setting the gate and bottle label input switches 306 to a two digit number which determines the offset from the beginning of the table, i.e., "00" will result in the display of the first 80 bars, whereas 88 will display the last 80 bars from a table. Since two lines are stored at every memory address, the offset represents two table values (digitized lines) per increment. With the table number portion of the label input 306 being set to the table number desired, the NEXT and CHART switches 316 and 312 are depressed to display the 80 lines of the table. To print out a complete bar chart, a printer is connected to the print port on the rear panel of the computer and when set, the bar chart for the library table identified by the label input switches 306 will be printed out by depressing NEXT and PRINT switches 316 and 315.

Figure 23:
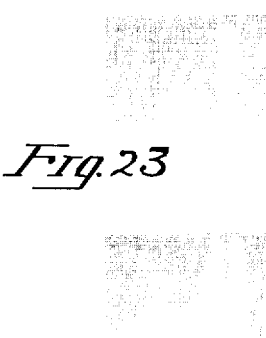
FIGS. 21, 22 and 23 present the major portion of the bar charts of FIGS. 18 through 20 respectively.
Figure 22:
Figure 21:

Referring again to FIGS. 18 through 20, characteristics of the bar charts may be noted. The main portions of the bar charts themselves from FIGS. 18 through 20 are reproduced in FIGS. 21 through 23 in approximate alignment so as to better emphasize the similarities and differences in the charts. FIGS. 18 and 19 (and associated FIGS. 21 and 22) illustrate the similarities in the labels for 7UP and Diet 7UP and the corresponding similarities in the bar charts. It will be noted from FIG. 18 that the regular 7UP bottle has the words "Easy Open" relatively high on the neck, whereas the Diet 7UP bottle does not. In addition, the 7UP logo of the regular 7UP bottle is smaller and slightly lower on the Diet 7UP bottle, with the word "Diet" appearing thereabove. While these differences clearly provide bar charts of some differing character, it will be noted, particularly from FIGS. 21 and 22, that the common portions will not necessarily be read identically in each case, and the accumulated differences in the common portions may more than offset the smaller regions of difference in some instances, thereby resulting in a misidentification of a 7UP bottle as a Diet 7UP bottle or vice versa. Obviously bottle rotation will also have some effect on each of the bar charts, and since the bottles are not aligned in any particular angular orientation in the preferred embodiment, sorting of bottles as close in appearance to each other as 7UP and Diet 7UP bottles may have some associated error therewith using the correlation technique hereinbefore described. It is apparent however, in comparing the Sprite bottle bar chart with the bar charts of the 7UP bottles, that bottles of substantially different visual appearance in the the label region will be clearly and accurately identified using the prior correlation technique.

In the preferred embodiment, in order to avoid possible errors as hereinbefore described, the program of appendix A for carrying out all of the operations hereinbefore described further includes instructions for testing the margin between the best correlation, and the next best correlation of a different gate number as displayed on display 332 of FIG. 25, and if that margin is less than a predetermined comfortable amount (ten percent in the preferred embodiment), a second correlation is done under software control between the two top contenders to finally determine which of the library tables truly corresponds to the target bottle. This second correlation, the program for which is attached hereto as Appendix B, makes use of the fact that while no final decision was made as a result of the first correlation, certain facts are taken as having been determined by that correlation. Specifically, the two top contending bottle types (library table numbers) have been identified. In addition, while 16 correlations of each of these two library tables with the target table were done using the 15 different precess values hereinbefore described, the precess values (offsets) giving the best correlations were retained, and accordingly are now known for the purposes of the second correlation.

The first correlation, as may be readily seen by examination of the theory thereof, emphasizes the similarities in bottle lables, so that a quick and accurate distinction can be made between labels having few similarities. However, in trying to distinguish between bottles having substantial similarities, such as 7UP and Diet 7UP, the small differences in the detection of the regions of similarity, because of the quality of the label print, bottle angle, etc., may accumulate so as to obscure the effect of small regions of great difference. Thus the second correlation is chosen to emphasize the differences in the labels as opposed to the similarity. In particular, the second correlation, utilizing the offsets determined in the first correlation, does a line by line recomparison of the target table with the "select" library table, and a line by line recomparison of the target table with the "reject" library table, in each case to find coincidence of nonzero data. A count is incremented if both lines have data, is unchanged if neither line has data and is decremented if only one line has data. The effect of this correlation is to find the similarity of data location (or lack thereof) thereby discriminating against the label elements appearing in only one table. Obviously, this second correlation can be done quite quickly, even under program control, as the algorithm is very simple and only one pass is required for each of the two tables. The two results are compared and the table, gate and bottle identified as the higher of the two counts obtained, i.e., the higher correlation result.

Having now described the preferred embodiment of the present invention, various important aspects and variations of the invention can be seen. Various image analysis techniques have been proposed and some have been used for various purposes for some time. One of the primary advantages of the present invention however, is the fact that the initial input data for the image is immediately processed at very high speed to provide a substantial reduction in the amount of data for which successively lower speed analyses may be undertaken as the data analysis process becomes simpler. By way of example, in the present invention, the video image is digitized in real time and stored as a binary number (four bit number in the preferred embodiment) summarizing all data for that sweep line of the raster scan. Thus the first level of data compaction is a real time data compaction process. The second level of data compaction is done by the high speed correlator board which, though of relatively simple design, is much faster in execution of the compaction than could be done by a general purpose computer. The final level of compaction to the ultimate bottle and gate identification is done very quickly under program control, not because the general purpose computer is particularly fast, but because the data has already been so compacted at high speed that very little analysis remains for the final determination.

The system described herein in detail is a black and white system using a horizontal scan. Obviously, if desired or more appropriate for other applications, the video camera could be rotated 90 degrees to effectively provide a vertical scan system, or any other angle as desired. In addition, certain color features could be emphasized by color filtering of the substantially white light from the strobe and/or putting an appropriate filter over the camera lens. Further, if full color were needed or desired for a particular application, a rotating color filter system could be placed over the camera lens to successively provide three corresponding primary color images for separate analysis (in this case some programming change might be required in accordance with the predetermined basis for making decisions based upon the correlations from the three color images). In a low speed system of this type, perhaps three successive shots could be taken of a bottle or other object at the target position before it moved out of the camera field. In a faster system, the target could be momentarily stopped or slowed so that the three shots could be taken, or a rotating prism or other mechanism could be used to deliver a stationary image of the moving target to the camera for a sufficient length of time to obtain the three shots. In still other instances, only two color filters, or combinations of unfiltered or one or more filtered images might be used.

One technique to derive second correlation techniques is to analyze the family of bottles to be sorted and choose a second correlation technique based on the analyses. Also a number of correlation techniques may be programmed, each being particularly suited to resolving uncertainty between two specific bottles. By way of example, excellent results have been obtained in sorting 7UP and Diet 7UP bottles by merely taking the total counts in the upper one third of the image, thereby determining whether the words "easy open" are present or not. (Also, ill effects of strobe reflection can be minimized in all embodiments using a strobe by placing a polarizing filter over the strobe and a polarized filter over the camera lens, and rotating the filters to minimize glare in the monitor image).

The present invention has been described in relation to bottle sorting equipment in accordance with the function of the preferred embodiment thereof. It should be noted however that many other functions could be achieved with the system of the present invention, such as by way of example, inspection functions. In particular, the library tables, instead of being loaded with bottle images, might be loaded with data corresponding to the images of acceptable and unacceptable characteristics to provide an accept-reject function automatically. A specific example might be a label inspector for examining labels on containers moving on a conveyor to determine that the label was on straight, didn't have a corner folded over, etc., and to even read the label and perhaps identify the container to be sure that the proper label has been applied.

Figure 24:
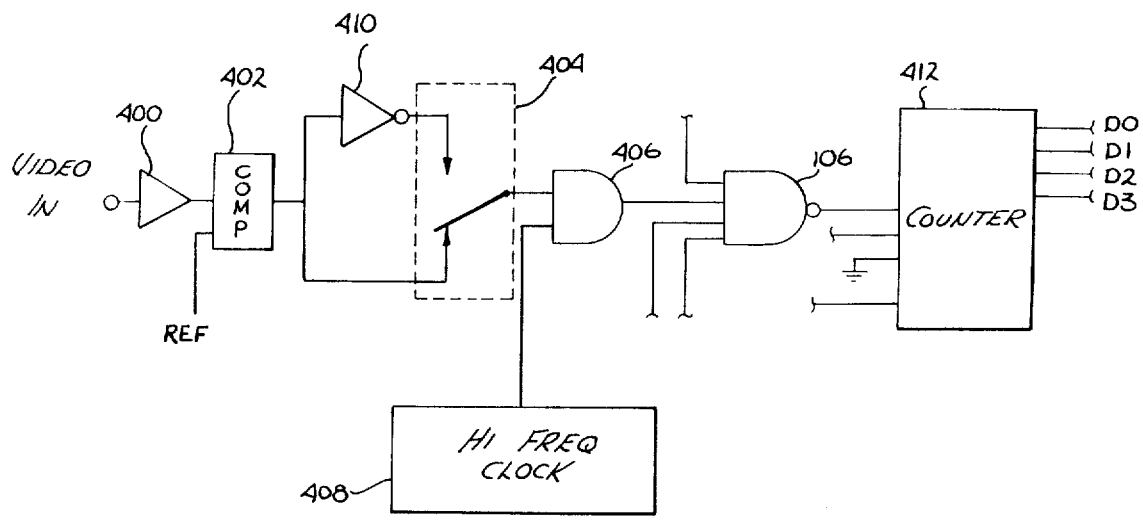
FIG. 24 is a schematic illustrating an alternate digitizing circuit.

It should be noted that the form of digitizer hereinbefore described is not the only form of digitizer which may be used with the invention to do the initial real time data compaction. By way of example, FIG. 24 presents a simplified schematic diagram illustrating another form of digitization which could be used with the bottle sorting machine hereinbefore described and which has certain characteristics which may make it more advantageous in other applications. In FIG. 7, the video signal on line 90 was amplified and differentiated by the NE 592 video amplifier with each light to dark transition providing a pulse output of the AT 20 high speed comparitor for counting by the counter 108 through NAND gate 106 for each sweep of the bottle image. In FIG. 24 the video signal is amplified by a video amplifier connected as an amplifier and not as a differentiator, and applied to a high speed comparitor 402. In this respect, the circuit may be very much like that of the corresponding portion of FIG. 7 except that the NE 592 video amplifier would not be connected as a differentiator. The output of the comparitor 402 is coupled through a switch 404 (preferably an electronic switch), not directly to the NAND gate 106, but through an additional AND gate 406, thereby effectively providing an enabling input to the AND gate. The other input of the AND gate 406 is provided by the high frequency clock 408 so that the corresponding input signal to the NAND gate 106 is a gated high frequency, as opposed to pulses representing transitions in the raster scan signal intensity. Switch 404 allows the switching between the direct output of the comparitor 402 and the output thereof as inverted by invertor 410, so that the gating signal to AND gate 406 may be selected as representing a given degree of lightness or a given degree of darkness of the corresponding region of the video image, as desired. The gated clock frequency output of NAND gate 106 is counted by counter 412 in much the same manner as counter 108 operates with respect to the embodiment of FIG. 7, though for reasons which shall subsequently be seen, a larger counter is preferred.

The concept and operation of the circuit of FIG. 24 is as follows: Assume by way of example that the circuit portion of FIG. 7 corresponding to that of FIG. 24 is replaced with the circuit of FIG. 24, and that the system as modified is used in the bottle sorting system hereinbefore described, with the 7UP bottle of FIG. 18 at the target position. Assume also that switch 404 is set so that the high frequency is gated to the counter 412 whenever the raster is scanning the light regions of the bottle image. Since the high frequency is gated to the counter during the sweep of the light regions, the total count of the counter for any sweep of the image will be proportional to the total length of light regions in that sweep. Thus, by way of example, with respect to the large horizontal P at the lower portion of the image of FIG. 18, the high frequency will be gated on a significant percentage of the sweep so that a bar chart of substantial height would result as opposed to the single light to dark transition that the previous embodiment would normally sense. The particular frequency used for the high frequency clock would determine the minimum width of a light region which could be sensed, which one might choose to be on the order of one percent of the length of each image scan line. Thus the frequency of the high frequency clock 408 might be chosen to provide on the order of 100 pulses or more during each sweep of the target image. Obviously if a four bit counter were used for counter 412, the total count would be truncated at 15. However, it is believed that in most applications it whould be better to use a larger counter and to take the four bit output therefrom as the four most significant bits of the total count for each sweep line. In this manner small light regions would contribute to the total count, even though their significance is less than one bit of the output from the counter used to provide the signals D0 through D3. By choosing an even higher clock frequency, an eight bit counter could be used for counter 412 to provide a scan sensitivity of one part in 256, even though the final result is truncated to one part in 16.

An examination of the image of the 7UP bottle of FIG. 18 and the image of the Sprite bottle of FIG. 20 will illustrate that the concept of the embodiment of FIG. 24 would function very well with respect to the bottle sorting task. The system of FIG. 24 may be particularly advantageous however, in certain inspection functions. By way of example, labels on pill bottles may be white labels on colored bottles. Such labels could be very easily inspected, using the embodiment described with respect to FIG. 24, as the bottle could be made to look black in image by filtering out the color of the bottle by an appropriate filter over the camera lens. Thus by appropriate adjustment of the reference voltage for comparitor 402, the width and position of the label can be measured, and labels which are skewed, have a corner folded over, are of the wrong size or missing altogether will be immediately sensed. In this regard, rejection might be based upon a correlation factor of less than a predetermined minimum level, such as 0.95, by better correlation with an unacceptable library image than is obtained for any acceptable library image, or a combination of both conditions to provide even greater flexibility in the inspection technique.

Obviously, the possibilities for use of the present invention are by no means limited to sorting or inspection tasks. By way of further example, there may be situations where parts are randomly oriented on a conveyor belt, though must be picked up automatically for automatic assembly equipment. The present invention could readily identify the angular or linear position or both of a part on a conveyor belt by comparing the image of the part, i.e., the target image, with prestored images of parts in various positions to determine the closest position to control the automatic handling equipment. Thus, while the present invention has been described with respect to certain preferred embodiments and uses thereof, it will be understood by those skilled in the art that various changes in form and detail may be made therein without departing from the spirit and scope of the invention.

EXHIBIT A

```
JM A000
A000  F3 31 00 E0 3A.00 DF FE AA C2:53 A0 3E 08 D3 10
A010  32 01 DF CD 8D.A0 DB 08 2F FE:14 CA 78 A0 FE 11
A020  CA D6 A0 FE 02.CA D9 A0 FE 01:CA DC A0 FE 12 CA
A030  DF A0 FE 08 CA.E2 A0 FE 18 CA:E5 A0 FE 04 CA E8
A040  A0 FE 40 CA EB.A0 FE 30 CA 00:AC FE 50 CA 03 AC
A050  C3 16 A0 DB 21.DB 22 AF 32 02:DF D3 11 D3 12 D3
A060  13 D3 14 D3 15.D3 16 D3 21 F6:80 D3 22 AF D3 22
A070  3E AA 32 00 DF.C3 0C A0 CD 9C:A0 21 00 80 01 00
A080  20 36 00 23 0B.79 BC C2 81 A0:C3 0C A0 DB 08 2F
A090  B7 C2 8D A0 3A.01 DF F6 40 D3:10 C9 3A 01 DF D3
A0A0  10 C9 3A 01 DF.F6 04 D3 10 3E:FF CD C5 A0 3A 01
A0B0  DF D3 10 C9 CD.A2 A0 F6 80 D3:10 DB 08 E6 20 C2
A0C0  BB A0 C3 00 A0.F5 3E 68 00 3D:C2 C8 A0 F1 3D F5
A0D0  C2 C6 A0 33 33.C9 C3 4A A1 C3:F6 A1 C3 13 A2 C3
A0E0  42 A2 C3 45 A2.C2 48 A2 C3 4B:A2 C3 4E A2 21 00
A0F0  DC 0E F0 3A 02.DF F6 01 D3 21:EE 01 D3 21 DB 08
A100  E6 20 CA 00 A0.DB 20 E6 01 C2:FE A0 DB 21 E6 40
A110  CA FE A0 DB 20.E6 01 C2 13 A1:DB 21 86 77 23 0D
A120  C2 13 A1 C9 DB.0C 2F CD 30 A2:FE 00 CA B4 A0 FE
A130  40 D2 B4 A0 6F.26 00 0E 07 29:0D C2 39 A1 11 00
A140  80 19 C9 E6 F8.1F 1F 1F 1F C9:CD 9C A0 CD 24 A1
A150  E5 11 78 00 19.4E DB 0D 2F 47:E6 F0 CA B4 A0 CD
A160  43 A1 FE 0A D2.B4 A0 78 E6 0F:CA B4 A0 FE 0A D2
A170  B4 A0 79 FE AA.C2 92 A1 CD A2:A0 CD 8D A0 CD 9C
```

```
A180  A0 DB 08 47 E6.10 CA 92 A1 78:E6 20 CA 00 A0 C3
A190  81 A1 21 00 DC.0E F0 36 00 23:0D C2 97 A1 06 10
A1A0  CD EE A0 3E C6.CD C5 A0 05 C2:A0 A1 21 00 DC 11
A1B0  00 00 0E F0 7E.CD 43 A1 CE 00:77 83 5F 3E 00 8A
A1C0  57 23 0D C2 B4.A1 E1 D5 11 00:DC 3E F0 0F 4F 1A
A1D0  07 07 07 07 47.13 1A 80 77 23:13 0D C2 CF A1 36
A1E0  AA 23 DB 0C 2F.77 23 DB 0D 2F:77 23 23 23 23 D1
A1F0  72 23 73 C3 00.A0 CD 9C A0 CD:24 A1 11 78 00 19
A200  7E FE AA C2 B4.A0 23 7E FE 00:CA B4 A0 2B 36 00
A210  C3 00 A0 CD 9C.A0 CD 24 A1 11:78 00 19 7E FE AA
A220  CA B4 A0 23 7E.FE 00 CA B4 A0:2B 36 AA C3 00 A0
A230  C5 47 E6 0F 4F.78 E6 F0 0F 47:81 4F 78 0F 0F 81
A240  C1 C9 C3 51 A2.C3 63 A2 C3 3C:A3 C3 94 A3 C3 29
A250  A4 CD 9C A0 CD.24 A1 0E 80 36:00 23 0D C2 59 A2
A260  C3 00 A0 CD 9C.A0 CD 24 A1 47:3E 10 D3 10 32 01
A270  DF C3 85 A2 CD.8D A0 DB 08 4F:E6 20 CA 00 A0 79
A280  E6 10 C2 77 A2.CD 9C A0 78 FE:40 DA 94 A2 CD A2
A290  A0 C3 00 A0 CD.34 A1 11 78 00:19 3E AA BE C4 A2
A2A0  A0 78 CD C4 A3.D3 11 23 23 7E:D3 12 04 C3 74 A2
A2B0  C5 7D 93 4F 7C.9A DA BC A2 81:C1 C9 C1 F6 01 37
A2C0  C9 7D 93 6F 7C.9A 67 DA BD A2:B5 C9 C5 01 09 00
A2D0  29 0D CA E9 A2.CD C1 A2 3F D2:E2 A2 78 17 47 C3
A2E0  DC A2 78 17 47.19 C3 D0 A2 B7:C1 C9 E5 C5 47 21
A2F0  17 A3 11 00 00.0E 09 0D CA 13:A3 78 17 47 DA 06
A300  A3 23 23 C3 F7.A2 7E 83 27 5F:23 7E 8A 27 57 23
A310  C3 F7 A2 C1 E1.B7 C9 00 50 00:25 50 12 25 06 13
A320  03 56 01 78 00.39 00 F5 DB 08:E6 20 CA 00 A0 DB
A330  6E E6 20 C2 28.A3 F1 D3 6F D3:16 C9 CD 9C A0 3E
A340  CD D3 15 AF D3.16 0E 28 DB 08:E6 20 CA 00 A0 3E
A350  FA CD C5 A0 0D.C2 48 A3 3E 3C:CD 27 A3 3E E6 CD
A360  27 A3 21 00 80.01 00 20 1E 00:7E CD 27 A3 83 5F
A370  23 0B 79 B0 C2.6A A3 7B CD 27:A3 CD A2 A0 C3 00
A380  A0 DB 08 E6 20.CA 00 A0 DB 6E:E6 10 C2 81 A3 DE
A390  6F D3 16 C9 CD.9C A0 3E CE D3:15 AF D3 16 3E 10
A3A0  D3 6E 1E 00 21.00 80 01 00 20:CD 81 A3 77 83 5F
A3B0  23 0B 79 B0 C2.AA A3 CD 81 A3:BB C2 B4 A0 CD A2
A3C0  A0 C3 00 A0 C5.06 00 D6 0A DA:D0 A3 04 C3 C7 A3
A3D0  C6 0A 4F 78 07.07 07 07 B1 C1:C9 3A 12 DF 21 04
A3E0  DF BE 3A 13 DF.23 C2 FC A3 BE:D8 0E 07 21 11 DF
A3F0  11 03 DF 7E 12.23 13 0D C2 F3:A3 C9 BE D2 16 A4
A400  21 0C DF BE D8.0E 07 21 11 DF:11 0A DF 7E 12 23
A410  13 0D C2 0D A4.C9 0E 07 21 03:DF 11 0A DF 7E 12
A420  23 13 0D C2 1E.A4 C3 EE A3 C3:DF A4 3A 01 DF F6
A430  40 D3 10 21 00.80 DB 08 2F FE:20 CA 00 A0 FE 10
A440  C2 51 A4 CD 8D.A0 3A 02 DF F6:01 D3 21 EE 01 D3
A450  21 DB 20 E6 01.C2 36 A4 DB 21:17 D2 60 A4 2E FF
A460  17 DA 68 A4 2C.C3 36 A4 CD 9C:A0 2C 7D FE F0 DA
A470  81 A4 DB 20 E6.01 C2 72 A4 DB:21 B7 F2 72 A4 AF
A480  6F B7 1F 6F B7.C2 8A A4 3E 78:4F 11 00 00 DB 20
A490  E6 01 C2 8E A4.DB 21 47 83 5F:3E 00 8A 57 78 17
A4A0  17 17 17 77 DB.20 E6 01 C2 A4:A4 DB 21 47 83 5F
A4B0  3F 00 8A 57 78.B6 77 23 79 BD:CA C6 A4 3E 78 BD
A4C0  CA CD A4 C3 8E.A4 21 7E 80 72:23 72 C9 DB 20 E6
A4D0  01 C2 CD A4 DB.21 B7 F2 CD A4:2E 00 C3 8E A4 3E
A4E0  20 D3 10 32 01.DF 3E 80 D3 22:AF D3 22 DB 22 CD
A4F0  2C A4 2A 7E 80.7C 65 6F 22 18:DF 0E 0E AF 21 03
A500  DF 77 23 0D C2.01 A5 06 01 3E:40 D3 22 AF D3 22
```

```
A510   78 FE 40 D2 7B,A5 CD 34 A1 11:78 00 19 DB 20 E6
A520   80 C2 1D A5 DB,22 32 15 DF E6:0F 57 DB 23 32 14
A530   DF 5F D5 4E 23,23 7E 32 1A DF:11 04 00 19 56 23
A540   5E 3E 40 D3 22,AF D3 22 79 B7:C2 51 A5 E1 C3 77
A550   A5 2A 18 DF CD,B0 A2 DA 5B A5:EB E1 CD CC A2 32
A560   13 DF 78 32 11,DF 3A 1A DF E6:F0 32 12 DF 21 00
A570   00 22 16 DF CD,DB A3 04 C3 10:A5 3E 80 D3 22 AF
A580   D3 22 CD A3 A5,21 00 00 22 1C:DF 3A 05 DF 21 0C
A590   DF 96 CD EC A2,7A D3 15 FE 10:7B D3 16 DA FC A7
A5A0   C3 E6 A4 3A 03,DF CD 34 A1 CD:C4 A3 D3 11 11 7A
A5B0   00 19 7E D3 12,E6 F0 D3 21 32:0? DF 3A 0A DF CD
A5C0   34 A1 CD C4 A3,D3 13 11 7A 00:19 7E D3 14 C9 00
A5D0   00 00 00 00 00,00 00 00 00 00:00 00 00 00 00 00
A5E0   00 00 00 00 00,00 00 00 00 00:00 00 00 00 00 00
A5F0   00 00 00 00 00,00 00 00 00 00:00 00 00 00 00 00
A600   00 00 00 00 00,00 00 00 00 00:00 00 00 00 00 00
A610   00 00 00 00 00,00 00 00 00 00:00 00 00 00 00 00
A620   00 00 00 00 00,00 00 00 00 00:00 00 00 00 00 00
A630   00 00 00 00 00,00 00 00 00 00:00 00 00 00 00 00
A640   00 00 00 00 00,00 00 00 00 00:00 00 00 00 00 00
A650   00 00 00 00 00,00 00 00 00 00:00 00 00 00 00 00
A660   00 00 00 00 00,00 00 00 00 00:00 00 00 00 00 00
A670   00 00 00 00 00,00 00 00 00 00:00 00 00 00 00 00
A680   00 00 00 00 00,00 00 00 00 00:00 00 00 00 00 00
A690   00 00 00 00 00,00 00 00 00 00:00 00 00 00 00 00
A6A0   00 00 00 00 00,00 00 00 00 00:00 00 00 00 00 00
A6B0   00 00 00 00 00,00 00 00 00 00:00 00 00 00 00 00
A6C0   00 00 00 00 00,00 00 00 00 00:00 00 00 00 00 00
A6D0   00 00 00 00 00,00 00 00 00 00:00 00 00 00 00 00
A6E0   00 00 00 00 00,00 00 00 00 00:00 00 00 00 00 00
A6F0   00 00 00 00 00,00 00 00 00 00:00 00 00 00 00 00
A700   00 00 00 00 00,00 00 00 00 00:00 00 00 00 00 00
A710   00 00 00 00 00,00 00 00 00 00:00 00 00 00 00 00
A720   00 00 00 00 00,00 00 00 00 00:00 00 00 00 00 00
A730   00 00 00 00 00,00 00 00 00 00:00 00 00 00 00 00
A740   00 00 00 00 00,00 00 00 00 00:00 00 00 00 00 00
A750   00 00 00 00 00,00 00 00 00 00:00 00 00 00 00 00
A760   00 00 00 00 00,00 00 00 00 00:00 00 00 00 00 00
A770   00 00 00 00 00,00 00 00 00 00:00 00 00 00 00 00
A780   00 00 00 00 00,00 00 00 00 00:00 00 00 00 00 00
A790   00 00 00 00 00,00 00 00 00 00:00 00 00 00 00 00
A7A0   00 00 00 00 00,00 00 00 00 00:00 00 00 00 00 00
A7B0   00 00 00 00 00,00 00 00 00 00:00 00 00 00 00 00
A7C0   00 00 00 00 00,00 00 00 00 00:00 00 00 00 00 00
A7D0   00 00 00 00 00,00 00 00 00 00:00 00 00 00 00 00
A7E0   00 00 00 00 00,00 00 00 00 00:00 00 00 00 00 00
A7F0   00 00 00 00 00,00 00 00 00 00:00 00 C3 00 A8 00
RESET
```

EXHIBIT B

```
JM A800
A800  C3 61 A8 FE 08,DA 11 A8 E6 07:83 5F 7A CE 00 57
A810  C9 85 6F 7C CE,00 67 C9 7E E6:F0 CD 43 A1 CD 43
A820  A8 32 1B DF 1A,E6 F0 CD 43 A1:CD 43 A8 CD 48 A8
A830  7E E6 0F CD 43,A8 32 1B DF 1A:E6 0F CD 43 A8 CD
A840  48 A6 C9 D6 01,D0 AF C9 E5 21:1B DF 86 CA 5F A8
A850  3E CA 5C A8 7E,B7 CA 5C A8 03:E1 C9 0B E1 C9 E1
A860  C9 3E AA 32 1C,DF 3E 2C D3 16:3A 03 DF CD 34 A1
A870  3A 07 DF CD 43,A1 CD 03 A8 3E:71 F5 01 00 00 CD
A880  18 A8 23 13 F1,3D CA 9D A8 F5:C3 7F A8 60 69 22
A890  08 DF 3A 0A DF,CD 34 A1 3A 0E:DF CD 43 A1 CD 03
A8A0  A8 3E 71 F5 01,00 00 CD 18 A8:23 13 F1 3D CA B5
A8B0  A8 F5 C3 A7 A8,60 69 22 0F DF:2A 08 DF 59 50 CD
A8C0  FE A8 CD E6 A8,D2 E6 A4 0E 07:21 03 DF 11 0A DF
A8D0  46 1A 77 78 12,23 13 0D C2 D0:A8 CD A3 A5 3E AA
A8E0  32 1D DF C3 E6,A4 7C B7 FA F5:A8 7A B7 F2 F1 A8
A8F0  C9 CD 80 A2 C9,7A B7 FA F1 A8:F6 01 37 C9 E5 D5
A900  7A B7 F2 0F A9,2F 57 7B 2F 5F:13 19 C3 12 A9 CD
A910  C1 A2 7C B7 7D,F2 1A A9 2F 3C:FE 64 DA 21 A9 3E
A920  63 CD C4 A3 D3,16 D1 E1 C9 00:00 00 00 00 00 00
RESET
```

We claim:

1. In a bottle sorting system, the improvement comprising
    video camera means for receiving at least one two-dimensional image of at least a visually distinctive portion of a target bottle within the field of view of said video camera and for providing a video signal in response thereto
    digitizing means coupled to said camera means for providing a first plurality of digital signals responsive to said video signal, each said digital signal summarizing, in digital form, the features of a respective portion of the target bottle
    storage means for storing second pluarlities of digital signals, each of said digital signals within one of said second pluralities of digital signals summarizing, in digital form, the features of a respective portion of a bottle of one of the predetermined types of bottle to be sorted; and
    correlation means for correlating said first plurality of digital signals with each of said second plurality of digital signals to identify which of said predetermined types of bottles the target bottle most closely correlates.

2. The improvement of claim 1 wherein each digital signal summarizing, in digital form, the features of a respective portion of the target bottle summarizes at least one raster scan line of the target bottle image.

3. The improvement of claim 2 wherein each digital signal summarizes, in digital form, the features of the target bottle is a binary coded digital signal.

4. The improvement of claim 1 wherein each digital signal summarizes, in digital form, the features of a respective portion of the target bottle in one raster scan line of the target bottle image.

5. The improvement of claim 4 wherein each digital signal summarizes, in digital form, the features of the target bottle is a coded digital signal.

6. The improvement of claim 1 further comprised of transport means for successively transporting bottles past a target position, whereby said video camera may receive an image of at least a visually distinctive portion thereof.

7. The improvement of claim 6 further comprised of a strobe light to illuminate a bottle at the target position whereby said video camera may receive a strobed image of each target bottle.

8. The improvement of claim 7 further comprised of a trigger means to trigger said strobe upon the arrival of a bottle at the target position.

9. The improvement of claim 8 wherein said trigger means is also a means for triggering said digitizing means whereby a new image is digitized for correlation.

10. The improvement of claim 7 further comprised of a polarizing filter over the lens of said video camera.

11. The improvement of claim 10 further comprised of a polarizing filter over said strobe to polarize the illumination of the target bottle.

12. The improvement of claim 11 wherein said polarizing filters are aligned to minimize reflections of the strobe light in the image received by said video camera.

13. The improvement of claim 1 wherein each said digitizing means is a means for sensing transitions in image intensity on the raster scan of said video camera and providing as each respective said digital signal, a signal responsive to the number of transitions in a predetermined portion of the raster scan.

14. The improvement of claim 13 wherein said predetermined portion of the raster scan is one line of said raster scan.

15. The improvement of claim 1 wherein said digitizing means is a means for sensing regions of particular intensity of the raster scan image and providing as each said digital signal, a signal responsive to the length of the regions of the particular intensity in a predetermined portion of the raster scan.

16. The improvement of claim 15 wherein said predetermined portion of the raster scan is one line of said raster scan.

17. The improvement of claim 1 further comprised of
means for determining the margin in correlations between the correlation obtained between a target bottle and a first predetermined type of bottle with which the digital signals best correlate, and the correlation obtained between the target bottle and a second predetermined type of bottle with which the digitized signals next best correlate, and
second correlation means for correlating said first plurality of digital signals with each of said second plurality of digital signals for said first and second predetermined types of bottles utilizing a correlation technique differing from the correlation technique used in the first correlation when the margin in correlation is less than a predetermined amount.

18. Inspection apparatus comprising
video camera means for receiving a two-dimensional an image of at least the portion of an article to be inspected within the field of view of said video camera and for providing a raster scan video signal in response thereto
digitizing means coupled to said camera means for providing a first plurality of digitized signals responsive to the said raster scan video signal, each digital signal summarizing, in digital form, the characteristic of a respective portion of the raster scan of the image of the article to be inspected
storage means for storing a second plurality of digital signals, each of said digital signals within said second plurality of digital signals summarizing, in digital form, the features of a respective portion of the raster scan of an image of a preselected article having the specific characteristic to be inspected for; and
correlation means for correlating said first plurality of digital signals with said second plurality of digital signals to determine the similarity in the article being inspected and the preselected article.

19. The inspection apparatus of claim 18 wherein said digitizing means is a means for providing said first plurality of digital signals during the raster scan of the image of the article being inspected.

20. The inspection apparatus of claim 19 wherein said first and second plurality of digitized signals are binary coded digital signals.

21. The inspection apparatus of claim 20 wherein said correlation means is a means for correlating said first and second plurality of digital signals after all of said first plurality of digital signals for the article being inspected have been determined by said digitizing means.

22. The inspection apparatus of claim 21 wherein said correlation means further includes precessing means for correlating said first and second pluralities of digital signals with various amounts of precess to accommodate locational differences in the article being inspected and the preselected article.

23. The inspection apparatus of claim 21 further comprised of transport means for successively delivering articles to be inspected to the field of view of said video camera, and utilization means responsive to said correlation means for effecting the disposition of the article being inspected.

24. The apparatus of claim 23 wherein said storage means is a means for storing second pluralities of digital signals, each of said digital signals within one of said second pluarities of digital signals summarizing in digital form, characteristics to be inspected for, and means responsive to said correlation means for effecting the disposition of the article being inspected.

25. The apparatus of claim 24 wherein said apparatus further includes means for storing said second pluralities of digital signals when preselected articles are placed within the field of view of said video camera, whereby the specific characteristics to be inspected for may be changed as desired.

26. The apparatus of claim 19 wherein said apparatus further includes means for storing said second plurality of digital signals when the preselected article is placed within the field of view of said video camera camera, whereby the specific characteristics to be inspected for may be changed as desired.

27. A method of inspecting articles comprising the steps of
(a) storing a first plurality of digital signals, each representing a summary of the features of the raster scan of an item to be inspected for
(b) placing the article to be inspected in view of a video camera to obtain a raster scan video signal responsive to the image of at least part of the article to be inspected
(c) digitizing the video signal to provide a second plurality of digital signals, each representing a summary of features of the article to be inspected as represented by a portion of the raster scan, and
(d) correlating the digital signals of step (a) and step (c) to determine the similarities thereof.

28. The method of claim 27 wherein said first and second digital signals are binary coded digital signals.

29. The method of claim 27 wherein step (a) comprises the step of storing a first pluralities of digital signals, each digital signal in each plurality representing a summary of the features of the raster scan of a respective item to be inspected for, and step (d) comprises the step of correlating the digital signals of step (a) and step (c) to determine which of the items to be inspected for the article to be inspected most closely conforms.

30. The method of claim 29 comprised of the additional steps of determining the margin of correlation between the article to be inspected and (i) the item to which said digital signals of said article best correlates, and (ii) the item to which said digital signals of said article next best correlates, and if that margin is less than a predetermined amount, performing an additional and different correlation using the digital signals for the items determining the margin.

31. The improvement of claim 1 wherein said video camera means is a means for receiving an image comprised of at least part of the label on the target bottle, and said digitizing means is a means for providing said first plurality of digital signals, each said digital signal summarizing, at least in part, and in digital form, the features of the respective part of the label on the target bottle.

32. The improvement of claim 31 wherein said correlation means further includes precessing means for correlating said first and second pluralities of digital signals with various amounts of precess to accommodate locational differences in the target bottle and the predetermined types of bottles.

33. The improvement of claim 32 further comprised of means for determining the margin in correlations between the correlation obtained between a target bottle and a first predetermined type of bottle with which the digital signals best correlate, and the correlation obtained between the target bottle and a second predetermined type of bottle with which the digitized signals next best correlate, and second correlation means for correlating said first plurality of digital signals with each of said second plurality of digital signals for said first and second predetermined types of bottles utilizing a correlation technique differing from the correlation technique used in the first correlation when the margin in correlation is less than a predetermined amount.

34. The improvement of claim 31 wherein said video camera means is a means for receiving an image comprised of at least part of a substantially opaque label on the target bottle.

35. The inspection apparatus of claim 34 wherein said correlation means further includes precessing means for correlating said first and second pluralites of digital signals with various amounts of precess to accommodate locational differences in the target bottle and the predetermined bottle types.

36. The improvement of claim 35 further comprised of means for determining the margin in correlations between the correlation obtained between a target bottle and a first predetermined type of bottle with which the digital signals best correlate, and the correlation obtained between the target bottle and a second predetermined type of bottle with which the digitized signals next best correlate, and second correlation means for correlating said first plurality of digital signals with each of said second plurality of digital signals for said first and second predetermined types of bottles utilizing a correlation technique different from the correlation technique used in the first correlation when the margin in correlation is less than a predetermined amount.

37. In a bottle sorting system, the improvement comprising video camera means for receiving an image of at least a visually distinctive portion of a target bottle within the field of view of said video camera and for providing a video signal in response thereto digitizing means coupled to said camera means for providing a first plurality of digitized signals responsive to said video signal, each digital signal summarizing, in digital form, the features of a respective portion of the target bottle storage means for storing second pluralities of digital signals, each of said digital signals within one of said second pluralities of digital signals summarizing, in digital form, the features of a respective portion of a bottle of one of the predetermined types of bottle to be sorted correlation means for correlating said first plurality of digital signals with each of said plurality of digital signals to identify which of said predetermined types of bottles the target bottle most closely correlates means for determining the margin in correlations between the correlation obtained between a target bottle and a first predetermined type of bottle with which the digital signals best correlate, and the correlation obtained between the target bottle and a second predetermined type of bottle with which the digitized signals next best correlate, and second correlation means for correlating said first plurality of digital signals with each of said second plurality of digital signals for said first and second predetermined types of bottles utilizing a correlation technique differing from the correlation technique used in the first correlation when the margin in correlation is less than a predetermined amount.

38. In a bottle sorting system, the improvement comprising video camera means for receiving an image of at least a visually distinctive portion of a target bottle within the field of view of said video camera and for providing a video signal in response thereto digitizing means coupled to said camera means for providing a first plurality of digitized signals responsive to said video signal, each digital signal summarizing, in digital form, the features of a respective portion of the target bottle storage means for storing second pluralities of digital signals, each of said digital signals within one of said second pluralities of digital signals summarizing, in digital form, the features of a respective portion of a bottle of one of the predetermined types of bottle to be sorted; and correlation means for correlating said first plurality of digital signals with each of said second plurality of digital signals to identify which of said predetermined types of bottles the target bottle most closely correlates, said correlation means further including precessing means for correlating said first and second pluralities of digital signals with various amounts of precess to accommodate locational differences in the article being inspected and each predetermined type of bottle.

39. Inspection apparatus comprising video camera means for receiving an image of at least the portion of an article to be inspected within the field of view of said video camera and for providing a raster scan video signal in response thereto digitizing means coupled to said camera means for providing a first plurality of digitized signals responsive to the said raster scan video signal, each digital signal summarizing, in digital form, the characteristic of a respective portion of the raster scan of the image of the article to be inspected storage means for storing a second plurality of digital signals, each of said digital signals within said second plurality of digital signals summarizing, in digital form, the features of a respective portion of the raster scan of an image of a preselected article having the specific characteristic to be inspected for correlation means for correlating said first plurality of digital signals with said second plurality of digital signals to determine the similarity in the article being inspected and the preselected article, said correlation means further including precessing means for correlating said first and second pluralities of digital signals with various amount of precess to accommodate locational differences in the article being inspected and the preselected article.

* * * * *